United States Patent [19]
Kriesel et al.

[11] Patent Number: 5,885,250
[45] Date of Patent: Mar. 23, 1999

[54] FLUID DELIVERY DEVICE WITH CONFORMABLE ULLAGE

[75] Inventors: Marshall S. Kriesel, St. Paul; Farhad Kazemzadeh, Bloomington; Matthew B. Kriesel, St. Paul, all of Minn.; William W.. Feng, Lafayette, Calif.; Steve C. Barber, Shorewood, Minn.; William J. Kluck, Hudson, Wis.

[73] Assignee: Science Incorporated, Bloomington, Minn.

[21] Appl. No.: 991,930

[22] Filed: Dec. 16, 1997

Related U.S. Application Data

[62] Division of Ser. No. 541,183, Oct. 11, 1995, Pat. No. 5,735,818.

[51] Int. Cl.⁶ .................................................. A61M 37/00
[52] U.S. Cl. .......................................... 604/132; 604/246
[58] Field of Search ................................... 604/131, 132, 604/151, 153, 246

[56] References Cited

U.S. PATENT DOCUMENTS

| | | | |
|---|---|---|---|
| 3,918,446 | 11/1975 | Buttaravoli | 128/133 |
| 4,380,234 | 4/1983 | Kamen | 604/130 |
| 4,505,702 | 3/1985 | Perry et al. | 604/209 |
| 4,619,652 | 10/1986 | Eckenhoff et al. | 604/415 |
| 4,753,651 | 6/1988 | Eckenhoff et al. | 604/896 |
| 4,886,499 | 12/1989 | Cirelli et al. | 4/131 |
| 5,176,662 | 1/1993 | Bartholomew et al. | 604/283 |
| 5,257,980 | 11/1993 | Van Antwerp et al. | 604/282 |
| 5,390,671 | 2/1995 | Lord et al. | 128/635 |

FOREIGN PATENT DOCUMENTS

WO9513838  5/1995  WIPO.

*Primary Examiner*—Corrine M. McDermott
*Attorney, Agent, or Firm*—James E. Brunton

[57] ABSTRACT

An apparatus for accurately infusing fluids into a patient at specific rates over an extended period of time. The apparatus is of a low profile, laminate or layered construction having a stored energy source in the form of a distendable membrane, which, in cooperation with the base of the apparatus, defines one or more fluid reservoirs, each having a fluid inlet and a fluid outlet. The apparatus further includes, a novel conformable ullage made of yieldable materials. The conformable ullage uniquely conforms to the geometry of elastomeric membrane as the membrane returns to its less distended configuration and in so doing can move between a central chamber and a toroidal chamber formed in the cover of the apparatus. This arrangement will satisfy even the most stringent medicament delivery tolerance requirements and will elegantly overcome the limitations of materials selection encountered in devices embodying solely a rigid ullage construction. Additionally, the infusion cannula of the apparatus is connected to the base in a novel manner which permits expeditious subdermal delivery to the patient via a cannula which extends generally perpendicularly relative to the base.

9 Claims, 16 Drawing Sheets

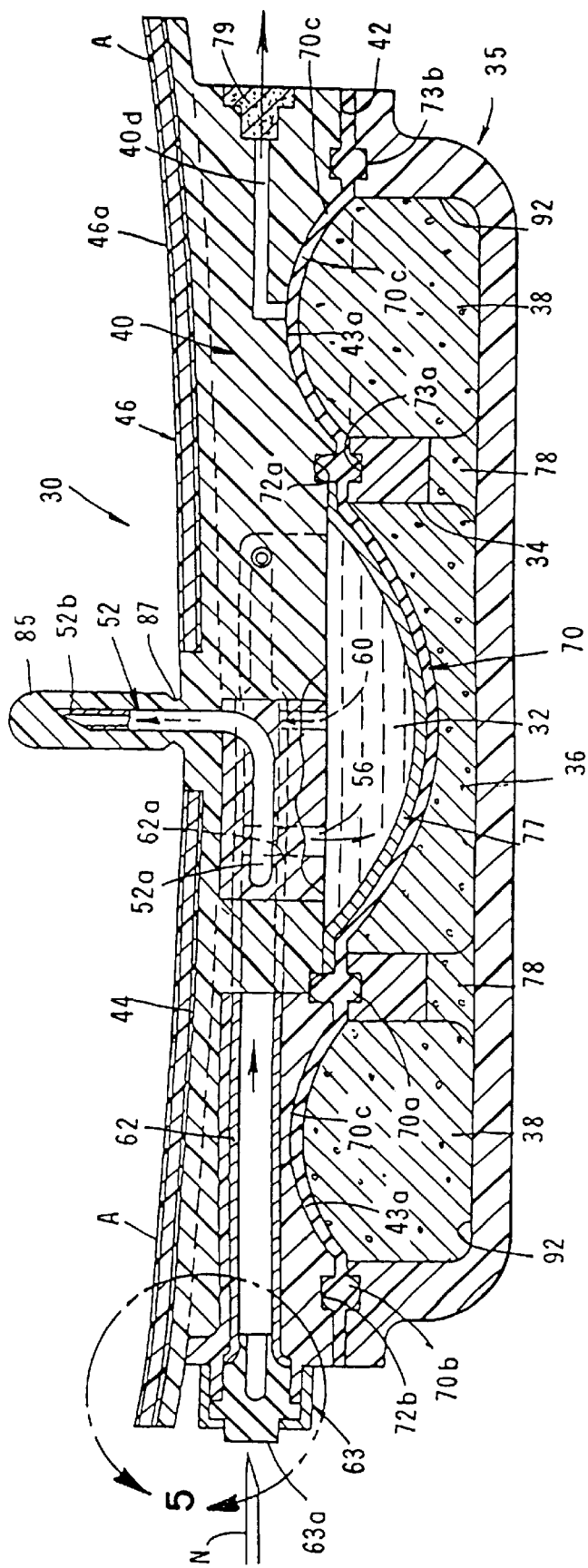
FIG. 3
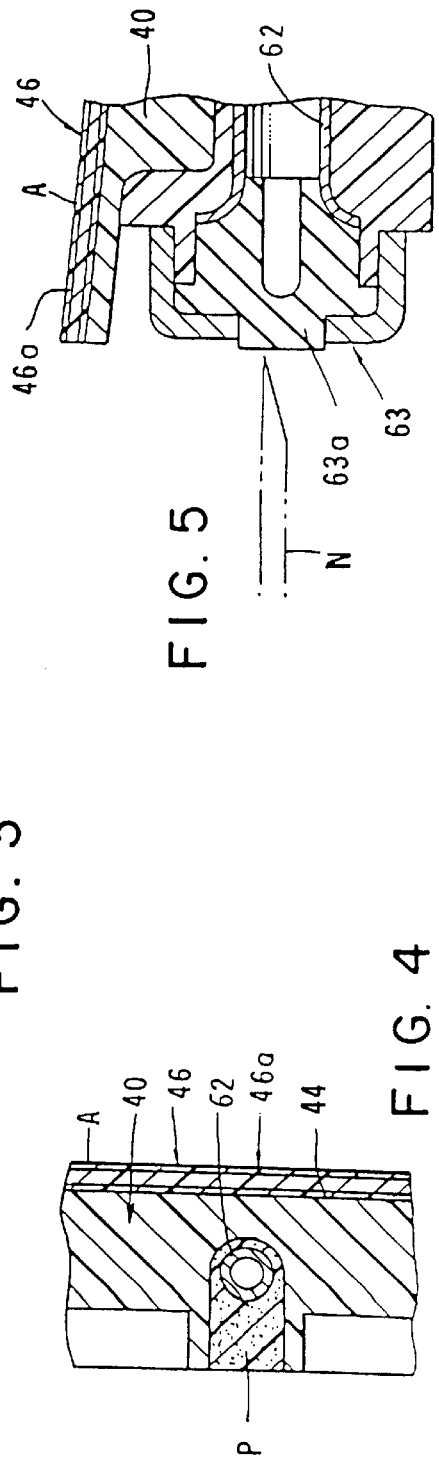
FIG. 5
FIG. 4

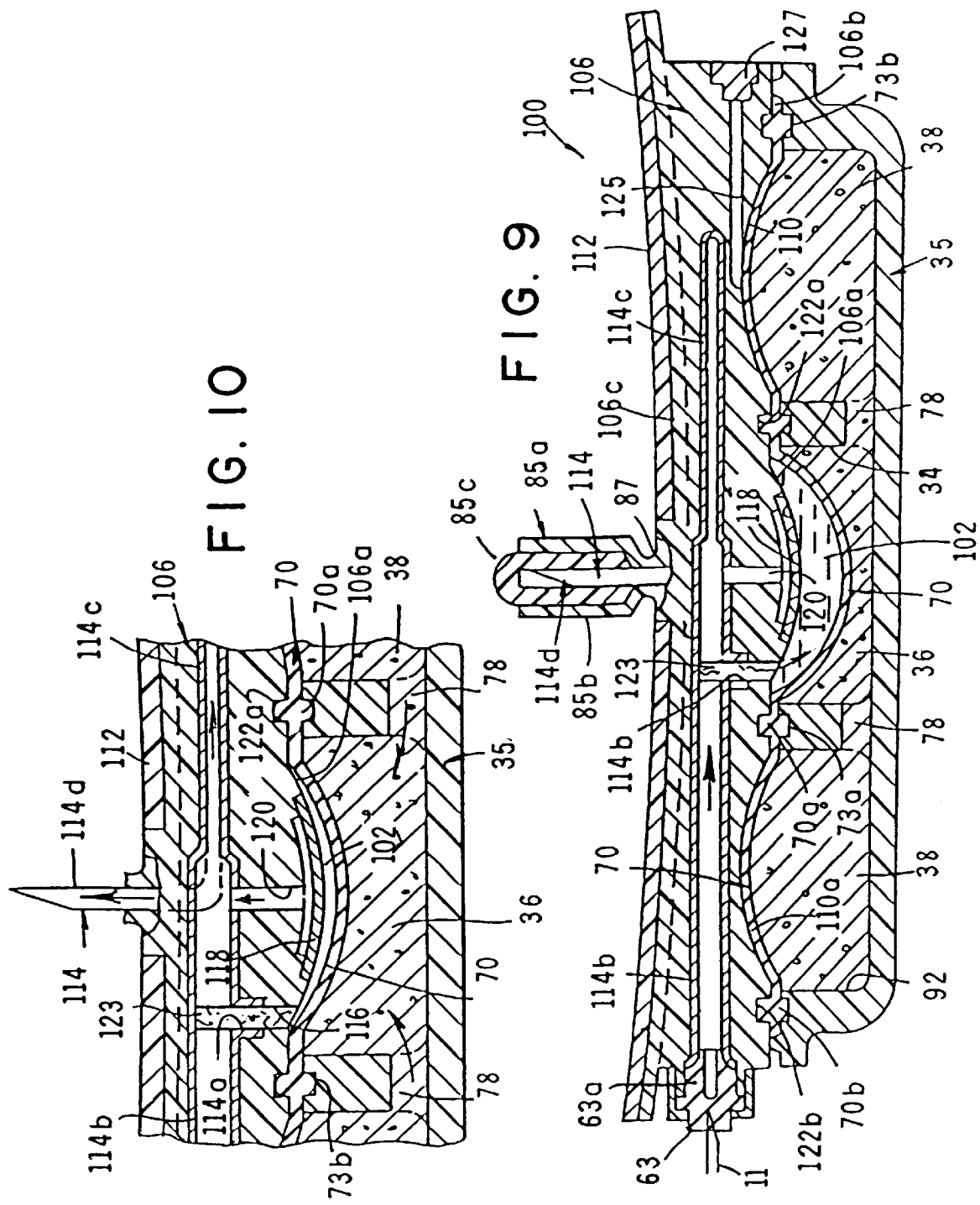

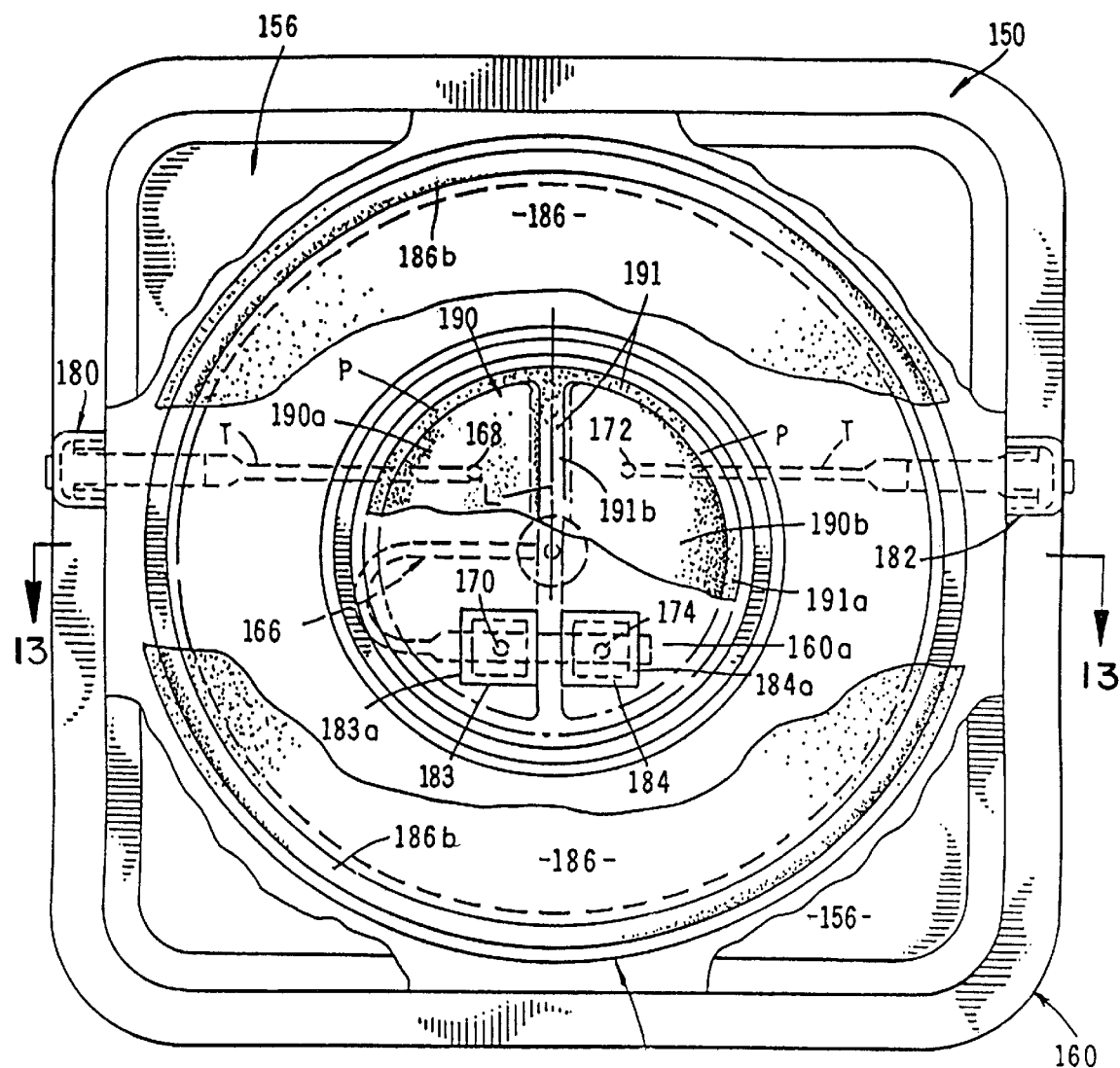
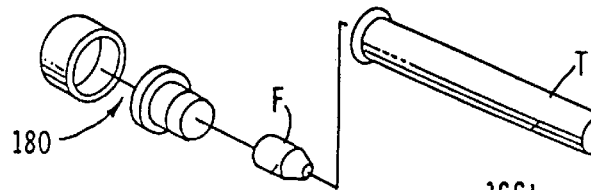
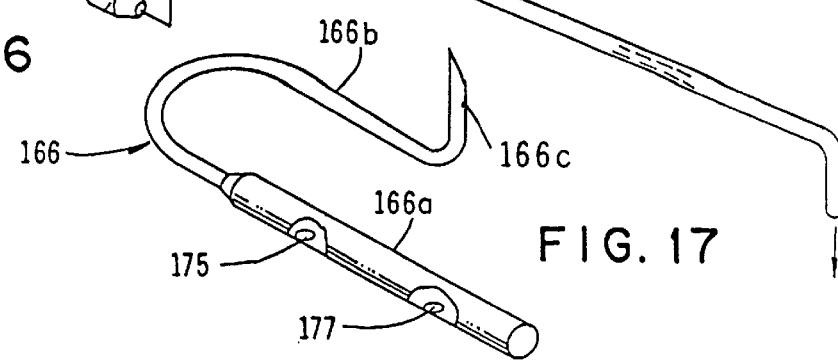
FIG. 11
FIG. 16
FIG. 17

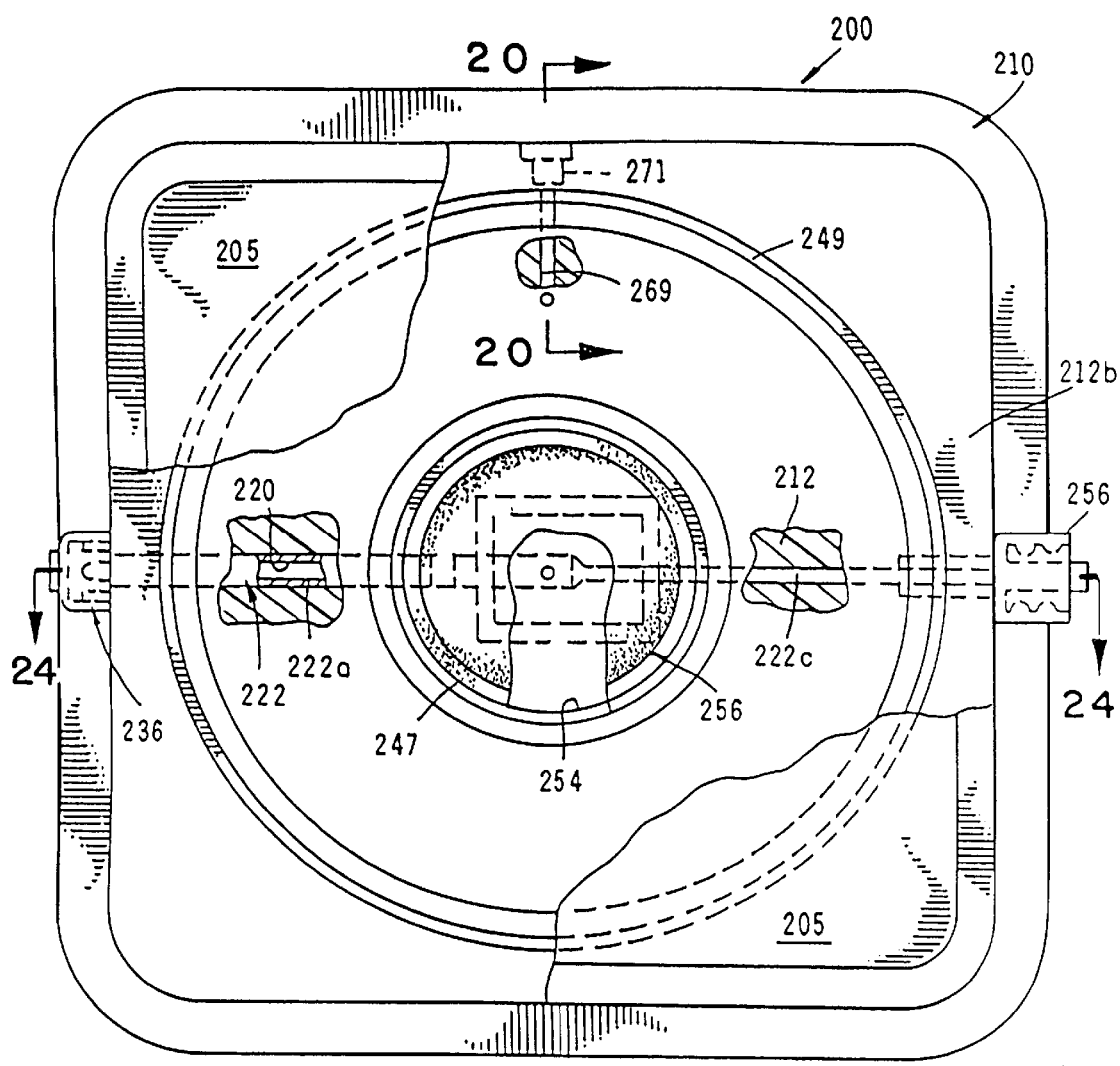
FIG. 18
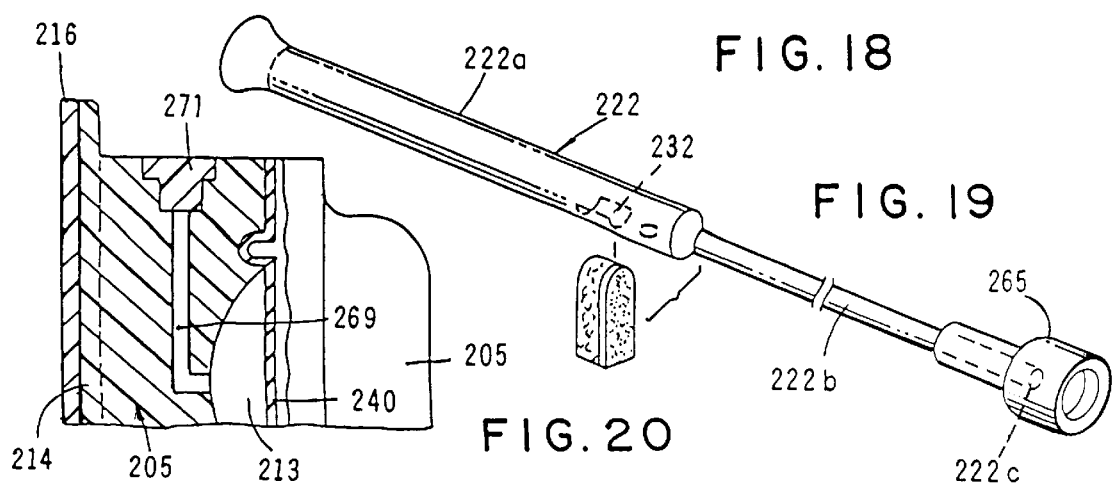
FIG. 19
FIG. 20

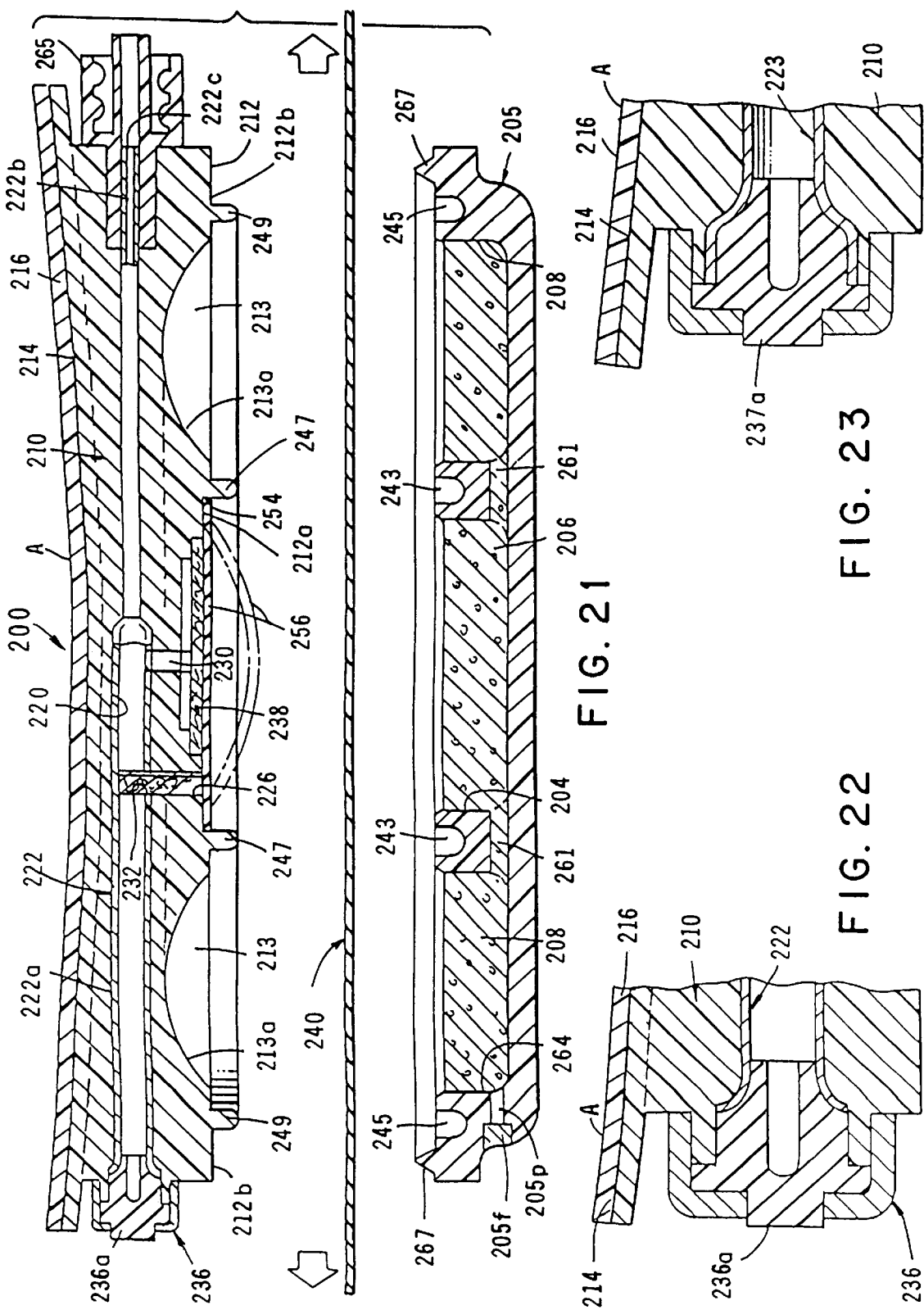

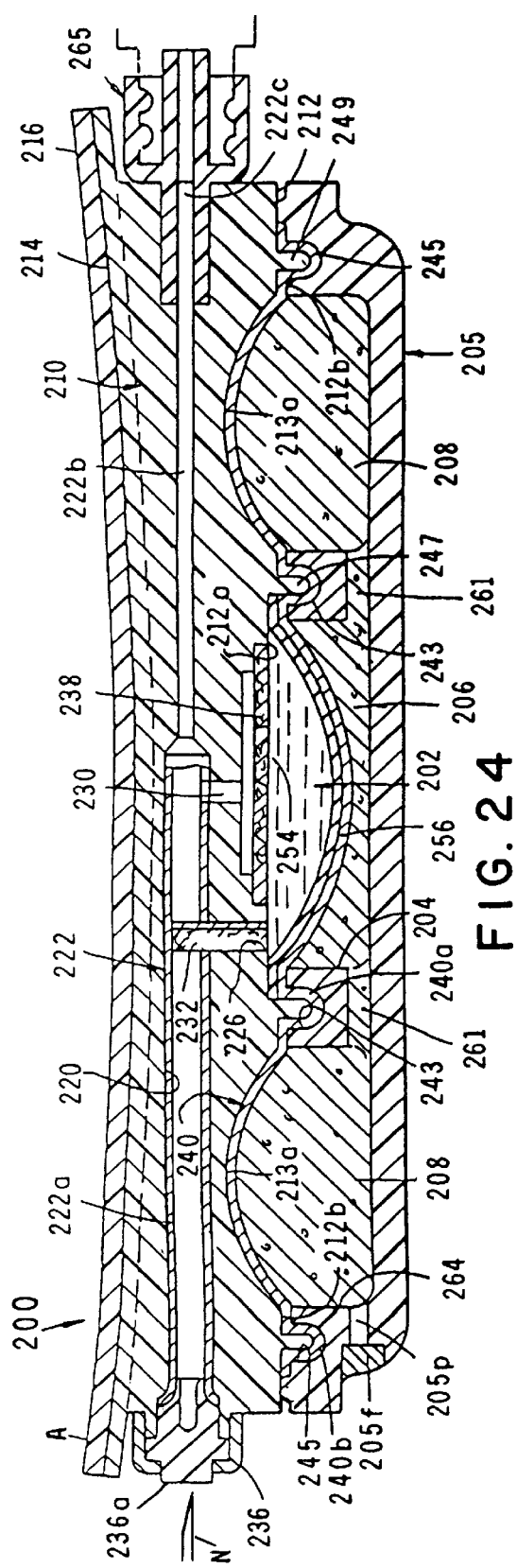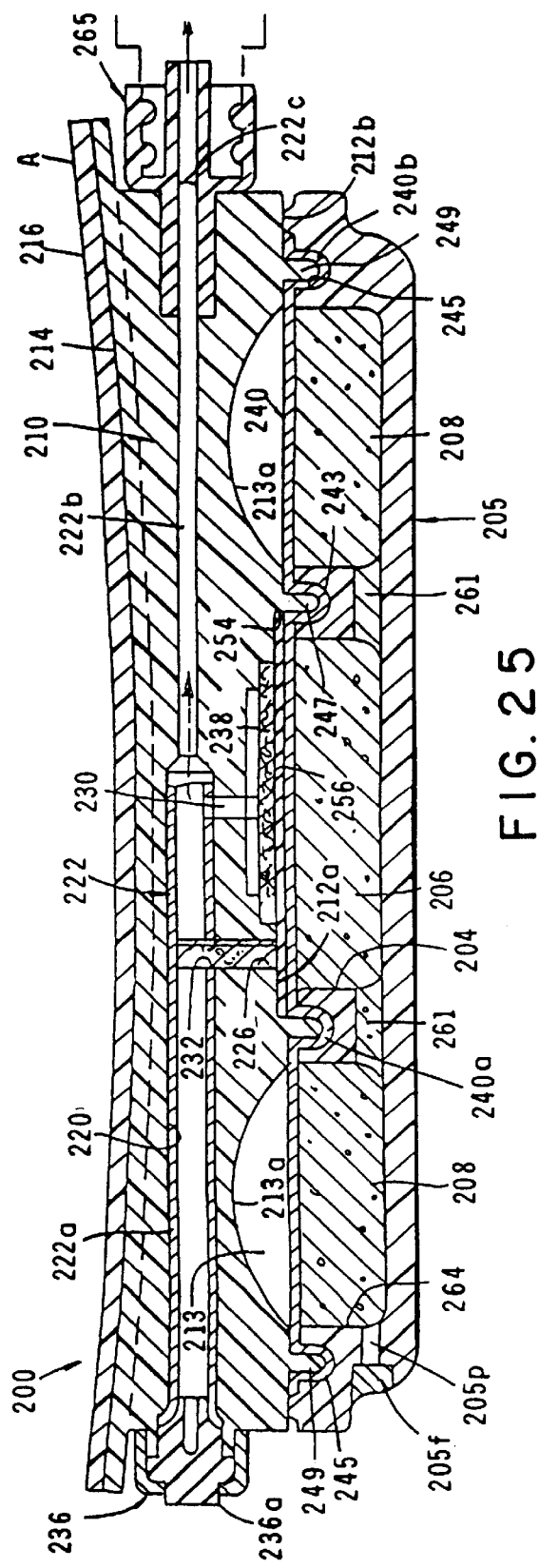

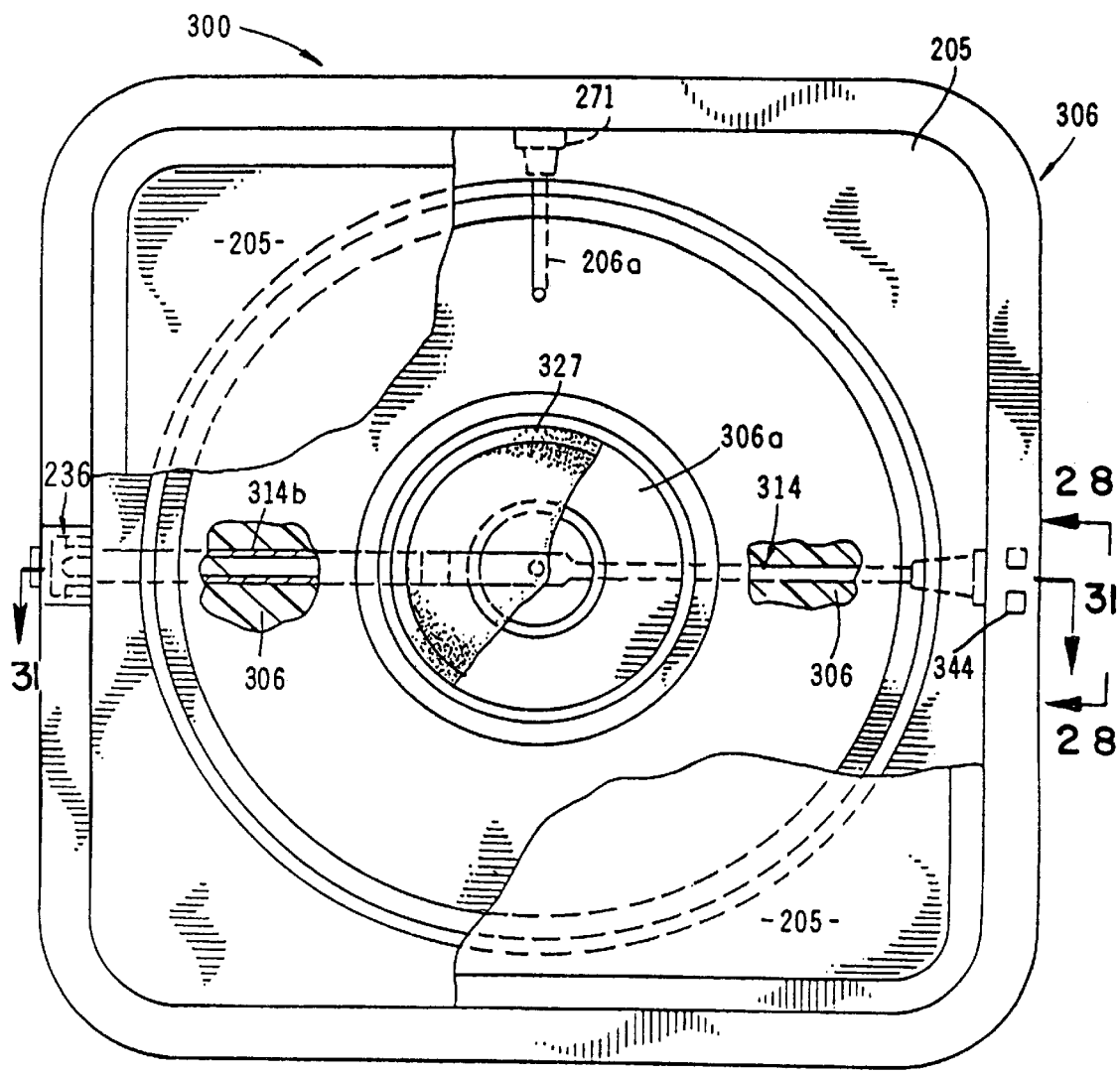
FIG. 26
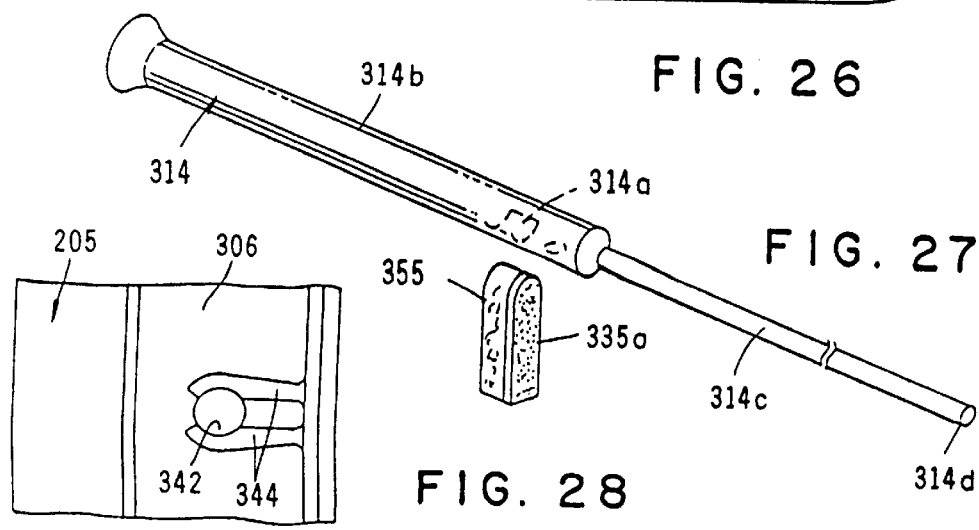
FIG. 27
FIG. 28

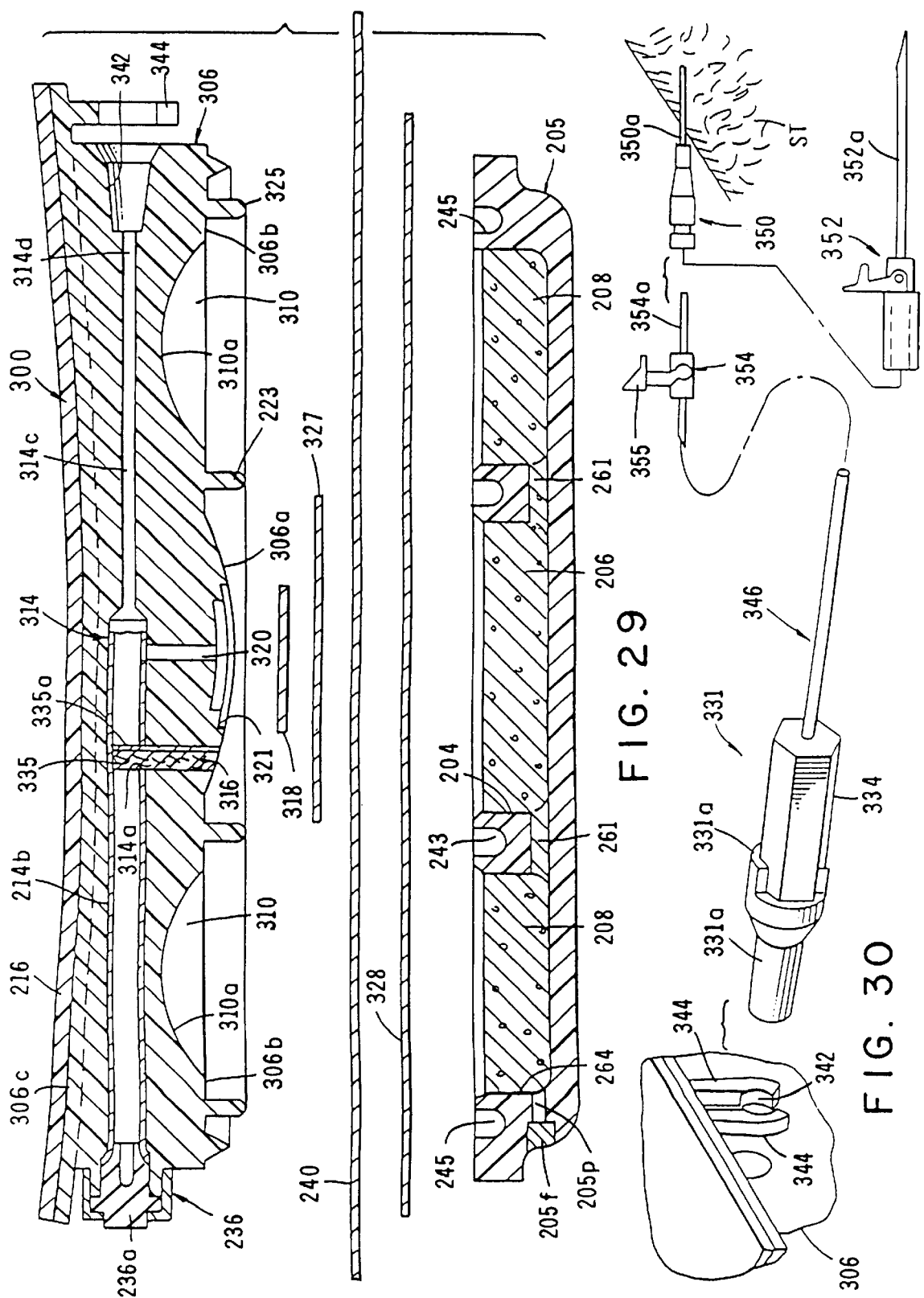

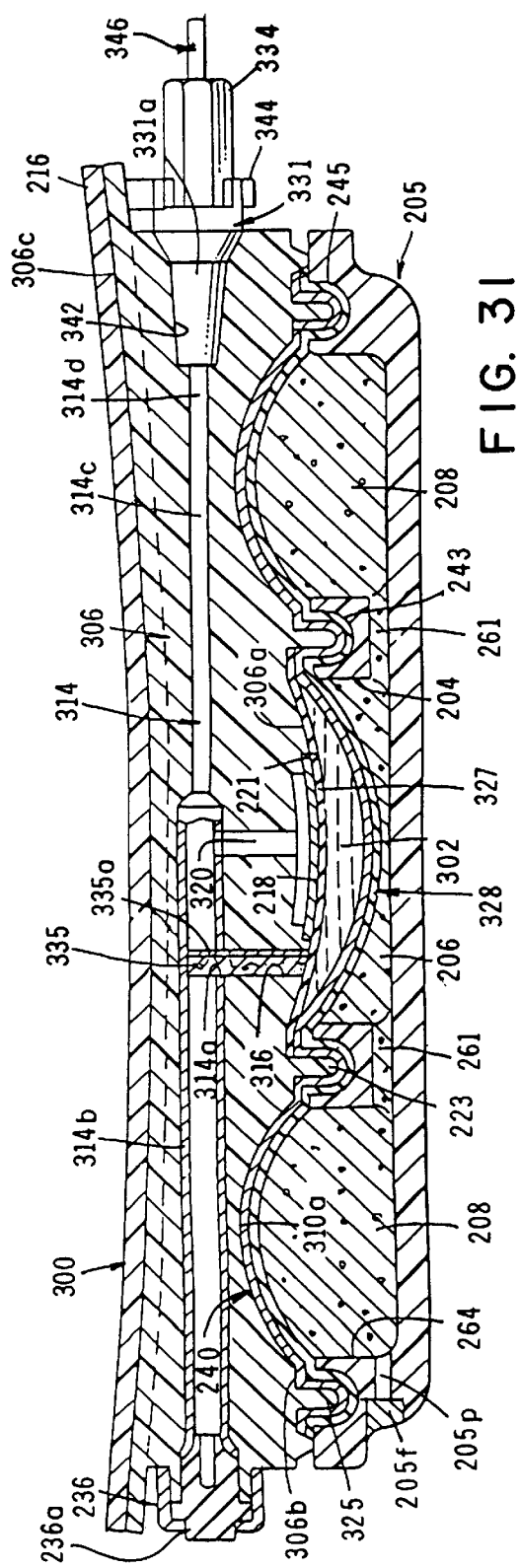
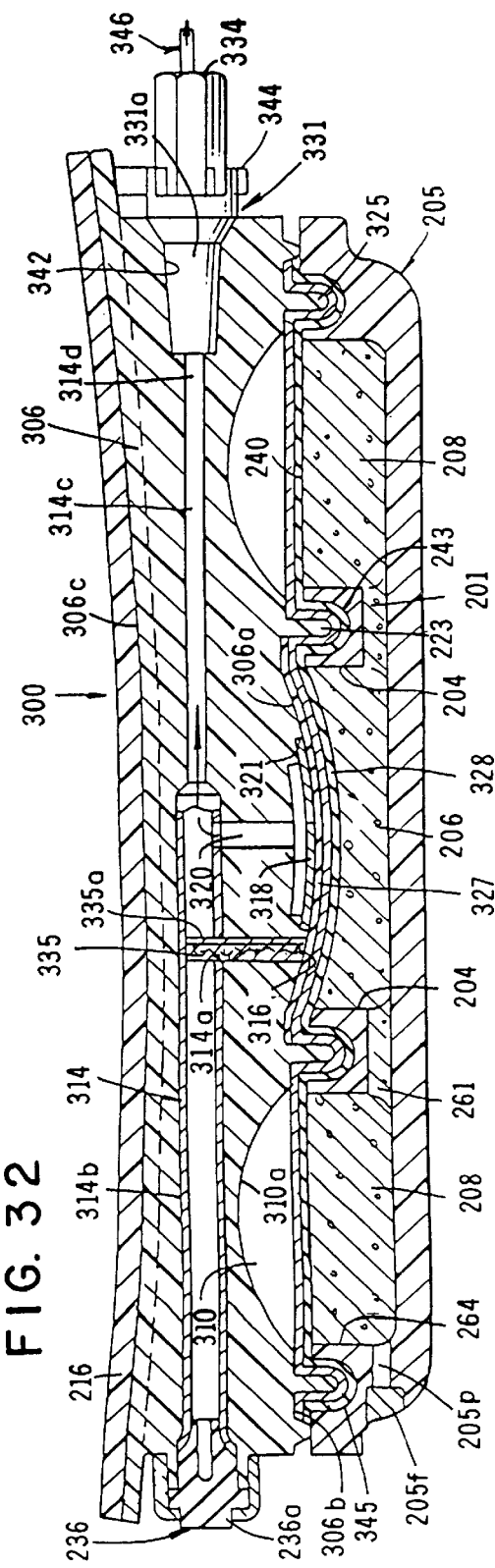
FIG. 31
FIG. 32

FLUID DELIVERY DEVICE WITH CONFORMABLE ULLAGE

This application is a divisional of application Ser. No. 08/541,183 filed Oct. 11, 1995 now U.S. Pat. No. 5,735,818, and is related to application Ser. No. 08/451,520 filed May 26, 1995 now U.S. Pat. No. 5,656,032 and is also related to a Continuation-In-Part application Ser. No. 08/540,914 filed on Oct. 11, 1995 now U.S. Pat. No. 5,716,343.

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time.

2. Discussion of the Invention

A number of different types of liquid dispensers for dispensing medicaments to ambulatory patients have been suggested. Many of the devices seek either to improve or to replace the traditional hypodermic syringe which has been the standard for delivery of liquid medicaments such as insulin solution.

Those patients that require frequent injections of the same or different amounts of medicament, find the use of the hypodermic syringe both inconvenient and unpleasant. Further, for each injection, it is necessary to first draw the injection dose into the syringe, then check the dose and, after making certain that all air has been expelled from the syringe, finally, inject the dose. This cumbersome and tedious procedure creates an unacceptable probability of debilitating complications, particularly for the elderly and the infirm.

One example of the urgent need for an improved liquid delivery device for ambulatory patients can be found in the stringent therapeutic regimens used by insulin-dependent diabetics. The therapeutic objective for diabetics is to consistently maintain blood glucose levels within a normal range. Conventional therapy involves injecting insulin by syringe several times a day, often coinciding with meals. The dose must be calculated based on glucose levels present in the blood. If the dosage is off, the bolus administered may lead to acute levels of either glucose or insulin resulting in complications, including unconsciousness or coma. Over time, high concentrations of glucose in the blood can also lead to a variety of chronic health problems, such as vision loss, kidney failure, heart disease, nerve damage, and amputations.

A recently completed study sponsored by the National Institutes of Health (NIH) investigated the effects of different therapeutic regimens on the health outcomes of insulin-dependent diabetics. This study revealed some distinct advantages in the adoption of certain therapeutic regimens. Intensive therapy that involved intensive blood glucose monitoring and more frequent administration of insulin by conventional means, for example, syringes, throughout the day saw dramatic decreases in the incidence of debilitating complications.

The NIH study also raises the question of practicality and patient adherence to an intensive therapy regimen. A bona fide improvement in insulin therapy management must focus on the facilitation of patient comfort and convenience as well as dosage and administration schemes. Basal rate delivery of insulin by means of a convenient and reliable delivery device over an extended period of time represents one means of improving insulin management. Basal rate delivery involves the delivery of very small volumes of fluid (for example, 0.5–3 mL. depending on body mass) over comparatively long periods of time (18–24) hours). As will be appreciated from the discussion which follows, the apparatus of the present invention is uniquely suited to provide precise fluid delivery management at a low cost in those cases where a variety of precise dosage schemes are of utmost importance.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly. The ullage in these devices, that is the amount of the fluid reservoir or chamber that is not filled by fluid, is provided in the form of a semi-rigid structure having flow channels leading from the top of the structure through the base to inlet or outlet ports of the device. Since the inventions described herein represent improvements over those described in U.S. Pat. No. 5,205,820 this patent is hereby incorporated by reference as though fully set forth herein.

In the rigid ullage configuration described in U.S. Pat. No. 5,205,820, wherein the ullage means is more fully described, the stored energy means of the device must be superimposed over the ullage to form the fluid-containing portion of the reservoir from which fluids are expelled at a controlled rate by the elastomeric membrane of the stored energy means tending to return to a less distended configuration in the direction toward the ullage. With these constructions, the stored energy membrane is typically used at high extensions over a significantly large portion of the pressure-deformation curve.

For good performance, the elastomeric membrane materials selected for construction of the stored energy membrane must have good memory characteristics under conditions of high extension; good resistance to chemical and radiological degradation; and appropriate gas permeation characteristics depending upon the end application to be made of the device. Once an elastomeric membrane material is chosen that will optimally meet the desired performance requirements, there still remain certain limitations to the level of refinement of the delivery tolerances that can be achieved using the rigid ullage configuration. These result primarily from the inability of the rigid ullage to conform to the shape of the elastomeric membrane near the end of the delivery period. This nonconformity can lead to extended delivery rate tail-off and higher residual problems when extremely accurate delivery is required. For example, when larger volumes of fluid are to be delivered, the tail-off volume represents a smaller portion of the fluid amount delivered and therefore exhibits must less effect on the total fluid delivery profile, but in very small dosages, the tail-off volume becomes a larger portion of the total volume. This sometimes places severe physical limits on the range of delivery profiles that may easily be accommodated using the rigid ullage configuration.

As will be better appreciated from the discussion which follows, the apparatus of the present invention provides an elongated, unique, disposable fluid dispenser of simple but highly reliable construction that may be adapted to a wide variety of end use applications. A particularly important aspect of the improved apparatus is the incorporation of conformable ullages made of yieldable materials which uniquely conform to the shape of the stored energy membrane as the membrane distends and then returns to a less distended configuration. The conformable ullages are uniquely contained within contiguous chambers and are free to move from one chamber to another as the stored energy membrane distends and then returns to a less distended configuration. This novel construction, which permits the overall height of the device to be minimized, will satisfy even the most stringent delivery tolerance requirements and uniquely overcomes the limitation of materials selection. Further, a plurality of subreservoirs can be associated with a single ullage thereby making it possible to incorporate a wide variety of delivery profiles within a single device.

Another useful liquid delivery device is that described in U.S. Pat. No. 5,226,896 issued to Harris. This device comprises a multidose syringe having the same general appearance as a pen or mechanical pencil. The device is specifically adapted to provide for multiple measured injections of materials such as insulin or human growth hormones.

Still another type of liquid delivery device is disclosed in U.S. Pat. No. 4,592,745 issued to Rex et al. This device is, in principle, constructed as a hypodermic syringe, but differs in that it enables dispensing of a predetermined portion from the available medicine and in that it dispenses very accurate doses.

The present invention seeks to significantly improve over the prior art by providing a novel fluid delivery device which is compact, is easy to use by ambulatory patients, and is eminently capable of meeting the most stringent of fluid delivery tolerance requirements.

SUMMARY OF THE INVENTION

It is an object of the present invention to provide an apparatus having a self-contained stored energy membrane for expelling fluids at. a precisely controlled rate which is of a compact, extremely low profile, laminate construction. More particularly, it is an object of the invention to provide such an apparatus which is of very low profile so that it can conveniently be used for the precise delivery of pharmaceutical fluids, such as insulin solution and the like, into an ambulatory patient at controlled rates over extended periods of time.

It is another object of the invention to provide an apparatus of the aforementioned character which is small, compact, highly reliable and easy-to-use by lay persons in a non-hospital environment.

It is another object of the invention to provide an apparatus as described in the preceding paragraphs which, can be used for intravenous infusion of fluids and, in a second form, can be used for subdermal infusion of fluids. In this regard, the apparatus includes a novel and unique delivery cannula having a body portion disposed within a circuitous channel formed within the base superstructure of the apparatus and a pierceable portion which extends outwardly from the base of the apparatus. The cannula is mounted within the circuitous channel in a manner such that the pierceable portion thereof extends generally perpendicularly from the base for easy insertion into the patient's arm, leg or other portions of the body.

Another object of the invention is to provide an apparatus which embodies a soft, pliable, conformable mass which defines an ullage within the reservoir of the device which will closely conform to the shape of the stored energy membrane thereby effectively avoiding extended flow delivery rate tail-off at the end of the fluid delivery period.

A further object of the invention is to provide a low profile, fluid delivery device of laminate construction as described in the preceding paragraph in which a centrally disposed conformable mass is free to move between a central chamber and a toroidal chamber formed in the cover of the device thereby permitting the device to meet even the most stringent fluid delivery tolerance requirements.

Another object of the invention is to provide an apparatus as described which includes a dual chamber fluid reservoir that permits controlled delivery of the same or different medicaments to the patient over time in a precisely controlled manner.

Another object of the invention is to provide an apparatus of the character described which includes novel fluid rate control means for precisely controlling the rate of fluid flow from the device.

Another object of the invention is to provide an apparatus which, due to its unique construction, can be manufactured inexpensively in large volume by automated machinery.

Other objects of the invention are set forth in U.S. Pat. No. 5,205,820 which is incorporated herein by reference and still further objects will become apparent from the discussion which follows.

BRIEF DESCRIPTION OF THE DRAWINGS

FIG. 3 is a cross-sectional view of the apparatus of FIG. 2 shown in an assembled configuration.

FIG. 4 is an enlarged cross-sectional view taken along lines 4—4 of FIG. 1.

FIG. 5 is an enlarged, cross-sectional view of the area designated as 5 in FIG. 3.

FIG. 9 is a cross-sectional view of the apparatus of FIG. 8 shown in an assembled configuration.

FIG. 10 is an enlarged, fragmentary cross-sectional view similar to FIG. 9 but showing fluid being expelled from the fluid reservoir of the device.

FIG. 11 is a top plan view of the base portion of still another form of the low profile infusion apparatus of the invention partly broken away to show internal construction.

FIG. 16 is an enlarged, generally perspective view of one of the filling subassemblies of the form of the invention shown in FIGS. 11 through 13.

FIG. 17 is an enlarged, generally perspective view of cannula assembly of the apparatus of the invention shown in FIGS. 11 and 12.

FIG. 18 is a top plan view of the base portion of yet another form of the low profile infusion apparatus of the invention partly broken away to show internal construction.

FIG. 19 is a generally perspective view of the cannula, septum assembly, and fluid outlet assembly of the latest form of the invention.

FIG. 20 is an enlarged, cross-sectional view taken along lines 20—20 of FIG. 18.

FIG. 21 is an exploded, cross-sectional view of the form of the invention shown in FIG. 18 illustrating the base portion of the apparatus superimposed over the rate control device, barrier member, the distendable membrane, and the cover of the apparatus.

FIG. 22 is a generally enlarged, fragmentary, cross-sectional view of the septum assembly of the invention shown in FIG. 21.

FIG. 23 is a greatly enlarged, fragmentary, cross-sectional view of an alternate form of the septum assembly.

FIG. 24 is an enlarged, cross-sectional view of the apparatus of FIG. 21 shown in an assembled configuration.

FIG. 25 is a cross-sectional view similar to FIG. 24, but showing fluid being expelled from the fluid reservoir of the device.

FIG. 26 is a top plan view of the base portion of yet another form of the low profile infusion apparatus of the invention partly broken away to show internal construction.

FIG. 27 is a generally perspective view of the cannula of this latest form of the invention.

FIG. 28 is an enlarged view taken along lines 28—28 of FIG. 26.

FIG. 29 is an exploded cross-sectional view of the form of the invention shown in FIG. 26 illustrating the base portion of the apparatus superimposed over the rate control device, the first barrier membrane, a second barrier membrane, the distendable membrane, and the cover of the apparatus.

FIG. 30 is an enlarged, generally perspective, exploded view of the fluid outlet subassembly of this latest form of the invention.

FIG. 31 is an enlarged, cross-sectional view taken along lines 31—31 of FIG. 26.

FIG. 32 is an enlarged, cross-sectional view similar to FIG. 31, but showing fluid being expelled from the fluid reservoir of the device.

DESCRIPTION OF THE INVENTION

Figure 1:
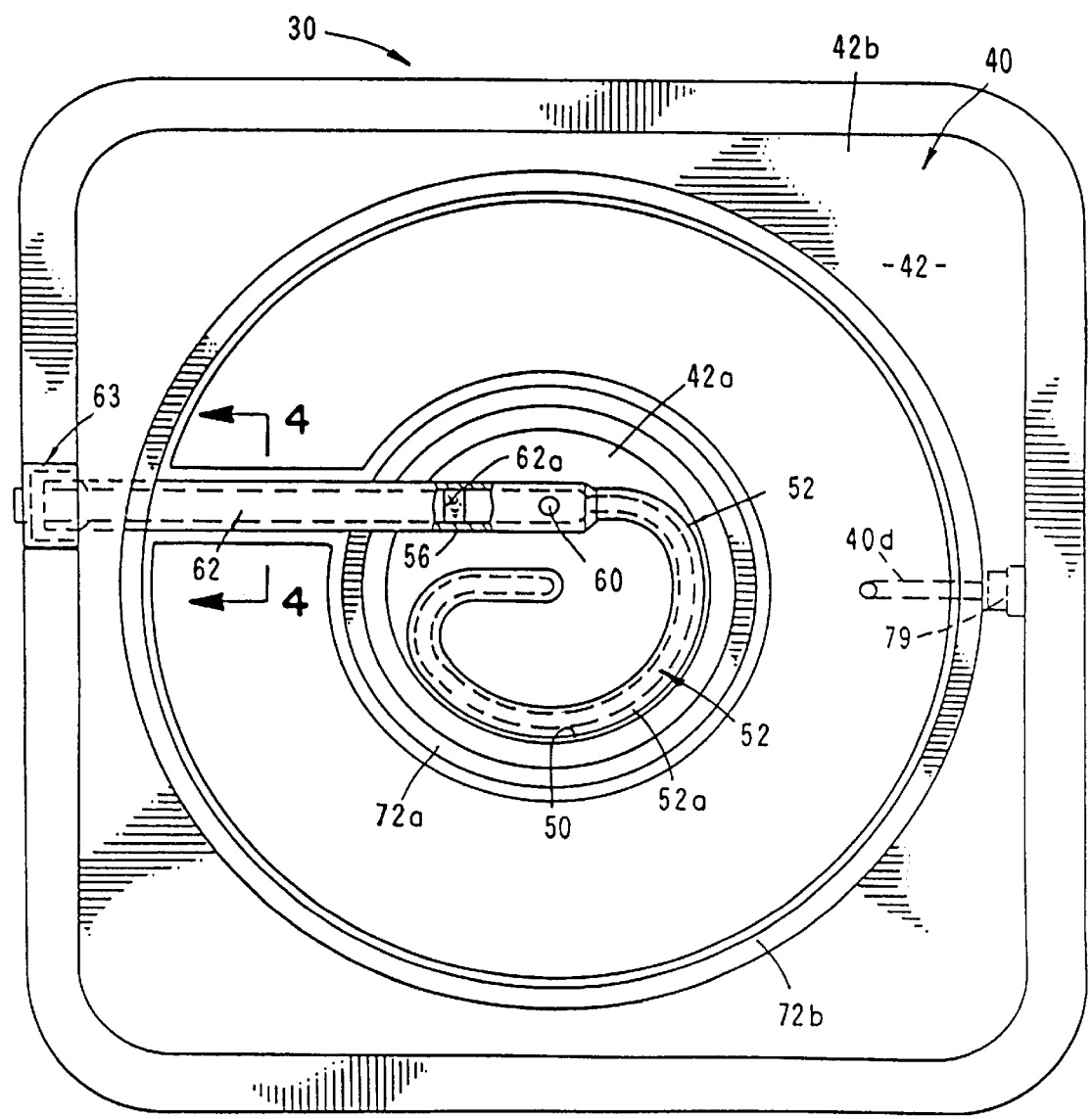
FIG. 1 is a top plan view of the base portion of one form of the low profile, subdermal infusion apparatus of the invention partly broken away to show internal construction.

Referring to the drawings and particularly to FIGS. 1 through 5, one form of the ultra low profile, expandable ullage fluid delivery device of the invention is there shown and generally designated by the numeral 30. As best seen in FIG. 3 this embodiment of the invention comprises a fluid reservoir 32 disposed within a central chamber 34 formed in a cover 35. Also disposed within central chamber 34 is a central conformable ullage, or first conformable mass 36 which is in an inferior position to central fluid reservoir 32 as the device is shown in FIG. 3. Cover 35 also includes a generally toroidal-shaped chamber 92 within which a generally toroidal-shaped second conformable mass or ullage 38 is disposed so that it circumscribes first mass 36.

Figure 2:
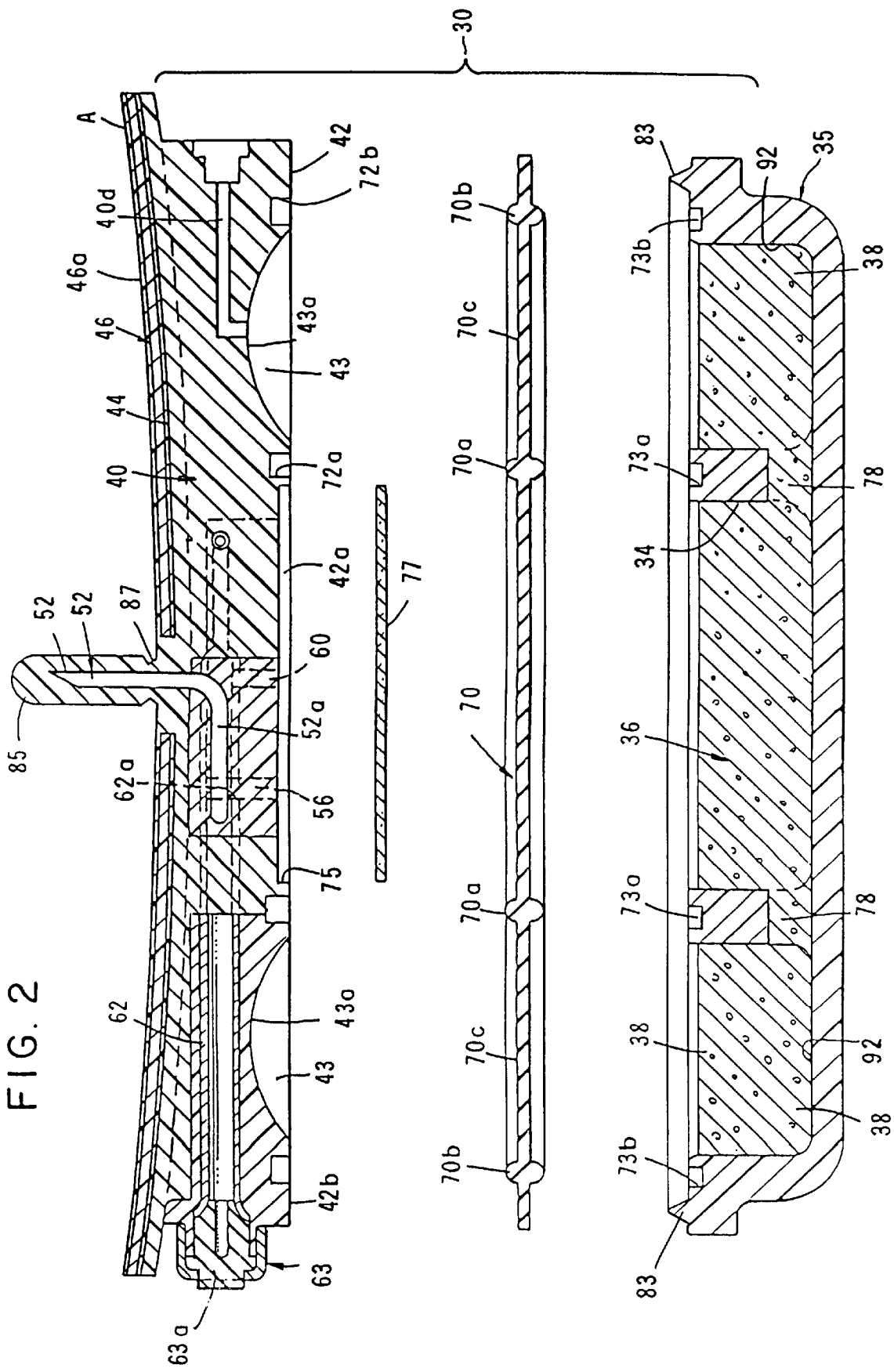
FIG. 2 is an exploded, cross-sectional view of the form of the invention shown in FIG. 1 illustrating the base portion of the apparatus superimposed over the barrier membrane, the distendable membrane and the cover of the apparatus.

The apparatus of the form of the invention shown in FIGS. 1 through 4 also comprises a base 40 having a first surface 42 which has a central portion 42a and a peripheral portion 42b circumscribing central portion 42a (FIG. 2). Peripheral portion 42b is provided with a circumferentially extending, concave surface 43a which defines a generally toroidal-shaped expansion channel or groove 43 formed within base 40. Base 40 is also provided with a second surface 44 to which an adhesive pad assembly 46 is affixed. After a peal strip 46a is removed from the pad assembly to expose an adhesive "A", the device can be affixed to the patient's body. Formed within base 40 is a circuitous channel 50 (FIG. 1), which receives a portion of the infusion means, or serpentine-shaped hollow cannula 52, of the invention.

The apparatus of this initial form of the invention also includes a uniquely configured stored energy means for forming, in conjunction with the central portion 42a of the base, the fluid reservoir 32. Fluid reservoir 32 has an inlet port 56 and an outlet port 60. Inlet port 56 is in communication with an outlet port 62a which is provided in an enlarged diameter portion 62 of cannula 52. Filling of fluid reservoir 32 is accomplished via a septum assembly 63 having a pierceable septum 63a (FIG. 5). A flow control means is also provided which here comprises the microbore portion 52a of the cannula which causes the fluid flowing into the enlarged diameter portion of the cannula via septum assembly 63 to flow through port 62a and toward reservoir 32.

The stored energy means is here provided in the form of a generally planar distendable membrane 70 which overlays surface 42 of the base. Membrane 70 includes an inner O-ring like protuberance 70a and a radially spaced, outer O-ring like protuberance 70b. These O-ring like protuberances form a part of the sealing means of the invention for sealably interconnecting base 40 and cover 35 and are sealably received within generally circular-shaped, radially spaced inner and outer O-ring grooves 72a and 72b formed in surface 42 of base 40 (see FIGS. 1 and 7). Grooves 72a and 72b also form a part of the sealing means of the invention. When the apparatus is assembled in the manner shown in FIG. 3, membrane 70 spans central portion 42a as well as the circumferentially extending grooved outer portion 42b of base 40. The inner and outer O-ring like protuberances are also sealably receivable within O-ring grooves 73a and 73b which are formed in cover 35 and which also comprise a part of the sealing means of the invention. Materials suitable for use in constructing the base, the cover and the distendable membrane are discussed in detail in U.S. Pat. No. 5,205,820 which is incorporated herein by reference.

Disposed within a generally circular shaped recess 75 formed in base 40 is a barrier or separation membrane 77 which prevents fluid within fluid chamber 32 from contacting distendable membrane 70. Membrane 77 can be formed from any suitable elastomeric material such as polyurethane, silicon or synthetic rubber.

With the construction shown in FIG. 3, the central or first conformable mass 36 of the ullage defining means is disposed within chamber 34 for engagement with membrane 70 which, after being distended, will tend to return to its less distended configuration. It is to be noted that both of the conformable masses 36 and 38 are uniquely covered by distendable membrane 70 and both continuously vary in shape as the distendable membrane distends outwardly from the base (FIG. 3).

A unique feature of this latest embodiment of the invention resides in the fact that the first conformable mass 36 communicates with the second, outer toroidal-shaped mass 38 via a plurality of passageways 78 which interconnect the first central chamber 34 formed in cover 35 with the second toroidal-shaped chamber 92 formed in cover 35 (FIG. 3). Conformable masses 36 and 38 preferably comprise a deformable, flowable mass constructed from a suitable gel material. Accordingly, in a manner presently to be described, the gel which makes up first conformable mass 36 can expand into chambers 92 formed in cover 35 via passageways 78 as the distendable membrane 70 distends outwardly during filling of fluid chamber 32.

Turning particularly to FIGS. 1, 2, and 3, the serpentine-shaped cannula 52 of the device includes the previously identified enlarged diameter portion 62 and the microbore portion 52a which terminates in a needle-like outboard extremity 52b. As best seen in FIG. 4, the enlarged diameter portion 62 of the cannula is held in position within channel 50 by a potting compound "P" of a character well known to those skilled in the art.

Turning particularly to FIG. 2, it can be seen that cover 35 is provided with an upstanding protuberance 83 which permits joining of the cover 35 to the base 40 by a sonic welding technique of a character understood by those skilled in the art. Prior to joining the cover and the base and, prior to positioning the distendable membrane over the cover, chambers 34 and 92 are filled with gel. Also, barrier membrane 77 is, at this time, be appropriately bonded to the base along its periphery by adhesive bonding or like techniques. When the cover and base are sealably joined together, the O-ring portions 70a and 70b are guided into sealable engagement with grooves 72a and 72b respectively so as to seal distendable membrane 70 relative to the base. If desired, a suitable adhesive can be placed within grooves 72a and 72b to bond the O-ring-like portions 70a and 70b to the base to enhance sealing. After the cover and base have been interconnected, conformable ullages 36 and 38 are sealably captured between distendable membrane 70 and the inner surfaces of cover 35 which define chambers 34 and 92.

Following the interconnection of base 40 with cover 35 in the manner described in the preceding paragraphs, fluid reservoir 32 can be filled via septum assembly 63 using a suitable syringe assembly containing the beneficial agent to be delivered to the patient. As the fluid chamber fills, conformable mass 36 will conform to the central portion of the distendable membrane in the manner shown in FIG. 3 causing the gel which comprises mass 36 to be forced inwardly and to overflow into the second toroidal-shaped chamber 92 via passageways 78. As the gel flows under pressure into chamber 92, the outer peripheral portion 70c of distendable membrane 70 will deform toward concave surface 43a and into base channel 43 permitting this channel to, at least, partially fill with gel. As the peripheral portion 70c of the distendable membrane 70 distends into channel 43, any gases contained therein will be vented to atmosphere via vent means which here comprises a passageway 40d and a vent plug 79 (see FIG. 3). With this novel construction, elevated fluid pressures within the fluid chamber 32 can readily be accommodated without having to increase the height of the chamber and, therefore, the overall height of the device. During the fluid expelling step, the gel can, of course, flow in the opposite direction from toroidal-shaped chamber 92 into first or central chamber 34 so as to conform to distendable membrane 70 as it tends to return toward its less distended configuration.

With chambers 34 and 92 filled with gel and with fluid reservoir 32 filled with the selected beneficial agent to be delivered to the patient, the device can be safely stored until time of use. At time of use, the novel needle protection means, or protective cover 85 can be broken away from base 40 along serration 87 (FIG. 3) and removed from the cannula thereby permitting fluid to flow outwardly of cannula end 52b.

Figure 6:
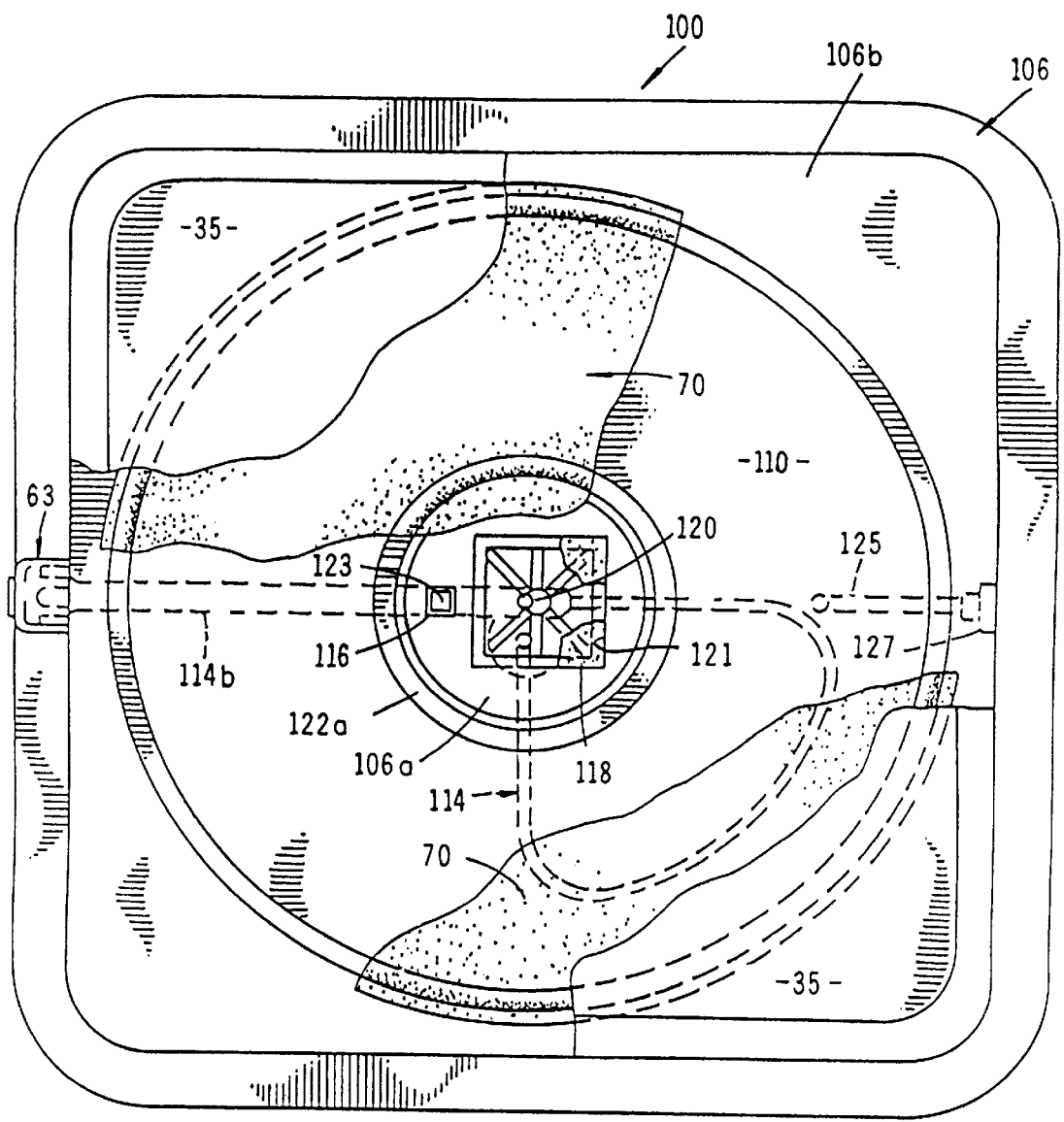
FIG. 6 is a top plan view of the base portion of another form of the low profile infusion apparatus of the invention partly broken away to show internal construction.
Figure 7:
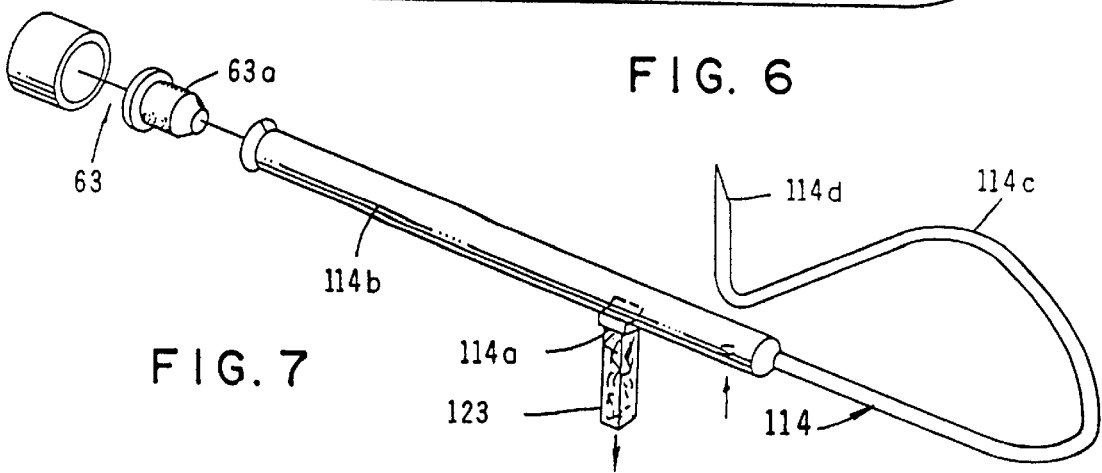
FIG. 7 is a generally perspective view of the cannula and septum assembly of this latest form of the invention.

Referring now to FIGS. 6 through 7, another form of the ultra low profile infusion device of the invention is there shown and generally designated by the numeral 100. This latest embodiment of the invention is similar in many respects to the embodiment shown in FIGS. 1 through 5 and like numbers are used to identify like components. This latest embodiment of the invention comprises a single fluid reservoir 102 (FIG. 9) disposed within a first central chamber 34 formed in a cover 35 which is identical to that previously described and includes conformable masses or ullages 36 and 38 of the character previously described which are in communication via passageways 78.

Figure 8:
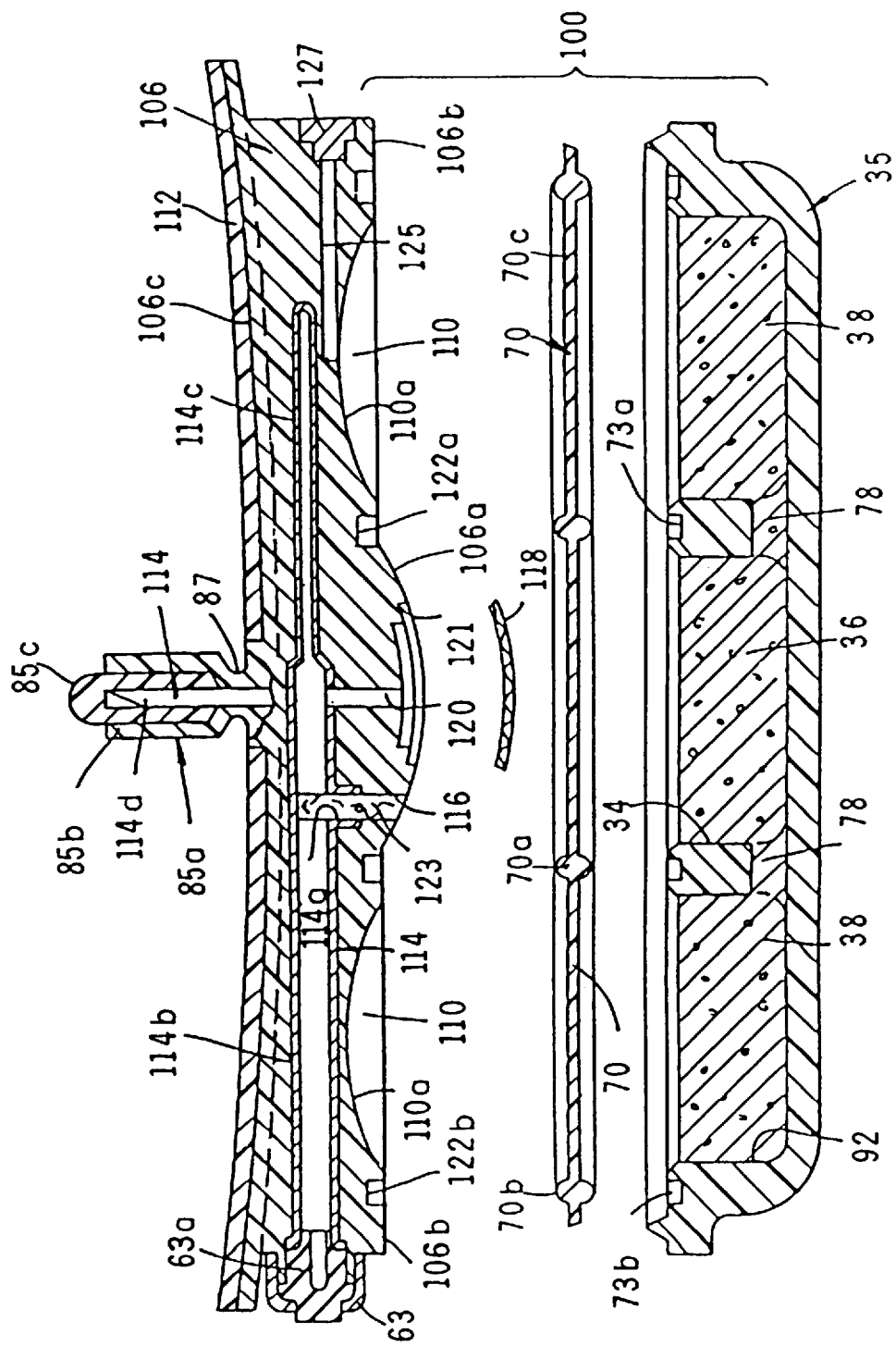
FIG. 8 is an exploded, cross-sectional view of the form of the invention shown in FIG. 6 illustrating the base portion of the apparatus superimposed over the rate control element, the distendable membrane, and the cover of the apparatus.

As best seen in FIGS. 8 and 9, base 106 of this embodiment is of a slightly different construction having a central, generally convex surface 106a and a peripheral portion 106b which includes a concave surface 110a which defines a generally toroidal-shaped expansion channel or groove 110 formed within base 106. In this latest form of the invention, convex portion 106a, in cooperation with conformable masses 36 and 38, comprises the ullage means of the invention. As before, base 106 has a surface 106c to which an adhesive pad assembly 112 is affixed. Integrally molded within base 106 is a serpentine-shaped hollow cannula 114, which comprises a part of the infusion means of this form of the invention.

The apparatus shown in FIGS. 6 through 9 includes a uniquely configured stored energy means identical to that described in connection with the embodiment shown in FIGS. 1 through 5 and forms, in conjunction with the central portion 106a of the base, the fluid reservoir 102. Fluid reservoir 102 has an inlet port 116 and an outlet port 120. Inlet port 116 is in communication with an outlet port 114a which is provided in an enlarged diameter portion 114b of cannula 114. Filling of fluid reservoir 102 is accomplished via a septum assembly 63 of the character previously described having a septum 63a.

In this latest form of the invention, flow control means comprises both a uniquely shaped hydrogel rate control device 118 as well as the micro bore portion 114c of the cannula. Rate control device 118 is held in place within a recess 121 formed in base 106 by any suitable means such as adhesive bonding (FIG. 8). In use, the hydrogel rate control device swells upon imbibing fluid and functions to precisely control the rate of fluid flow from reservoir 102.

As in the earlier described form of the invention, the stored energy means or membrane 70, overlays the base and includes an inner O-ring like protuberance 70a and a radially spaced, outer O-ring like protuberance 70b. These O-ring like protuberances, which form apart the sealing means, are sealably received within generally circular-shaped, radially spaced inner and outer O-ring grooves 122a and 122b formed in base 106 (see FIGS. 8 and 9). As before, grooves 122a and 122b also form a part of the sealing means of the invention. When the apparatus is assembled in the manner shown in FIG. 9, membrane 70 spans the central portion of the base as well as the circumferentially extending grooved outer portion 106b. The inner and outer O-ring like protuberances are also sealably receivable within O-ring grooves 73a and 73b which are formed in cover 35 (FIG. 8) and which comprise a part of the sealing means.

In the construction shown in FIG. 9, the central concave portion 106a of the base forms the rigid ullage portion of the ullage means and ullage portions 36 and 38 form the conformable ullage portions of the ullage means. As before, the conformable ullage portions of the ullage means are covered by distendable membrane 70 and both continuously vary in shape as the distendable membrane distends outwardly from the base as fluid is introduced into reservoir 102 via the septum assembly. Once again, central conformable ullage 36 communicates with the outer toroidal ullage 38 via passageways 78 so that, as fluid chamber 102 is filled, the gel which makes up the central ullage is engaged by membrane 70 urging it outward and causing it to flow into chamber 92 of cover 35. This causes the gel contained within this chamber to, in turn, expand, along with membrane 70, into channel 110 formed in base 106 in the manner shown in FIG. 9.

Turning particularly to FIGS. 6 and 8, the serpentine-shaped cannula 114 of the device there illustrated includes the previously identified enlarged diameter portion 114b and the microbore portion 114c which terminates in a needle-like outboard extremity 114d. Cannula 114 is molded in place with a base 106 in a manner well known by those skilled in the art. Extremity 114d is protected by a protective cover 85a which is similar to the previously discussed cover 85. However, cover 85a includes an outer sheath 85b which is connected to base 106 along a serration line 87. Sheath 85b telescopically receives a removable plug 87c which closely surrounds extremity 114d of the cannula.

Prior to joining the cover and the base as by sonic welding and, prior to positioning the distendable membrane over the cover, chambers 34 and 80 are filled with gel. Also, rate control device 118 is, at this time, emplaced into cavity 121. When the cover and base are sealably joined together, the O-ring protuberances or portions 70a and 70b are guided into sealable engagement with grooves 73a and 73b respectively so as to seal distendable membrane 70 relative to the base. If desired, a suitable adhesive can be placed within grooves 73a and 73b to bond the O-ring-like protuberance 70a and 70b to the base to enhance sealing. After the cover and base have been interconnected, conformable ullages 36 and 38 are sealably captured between distendable membrane 70 and the inner surfaces of cover 35 which define chambers 34 and 92.

Following the interconnection of base 106 with cover 35 in the manner described in the preceding paragraphs, fluid reservoir 102 can be filled via septum assembly 63 using a suitable syringe assembly containing the beneficial agent to be delivered to the patient. Filter means, shown here as a porous filter 123, filters the fluid flowing out of outlet 114a. Filter 123 can be constructed from any suitable porous material such as a polycarbonate material. As the fluid chamber fills, the peripheral portion 70c of the distendable membrane 70 will distend into channel 110, and any gases contained therein will be vented to atmosphere via passageway 125 and vent plug 127 (see FIG. 9). During the fluid expelling step, the gel can, of course, flow in the opposite direction from toroidal chamber 92 into central chamber 34 so as to conform to distendable membrane 70 as it tends to return toward its less distended configuration.

Turning next to FIGS. 11 through 17, still another form of the ultra low profile infusion device of the invention is there shown and generally designated by the numeral 50. This latest embodiment of the invention is somewhat similar to the embodiment shown in FIGS. 6 through 10 and like numbers are used to identify like components. This latest embodiment of the invention uniquely comprises a dual chamber fluid reservoir 152 (FIG. 13) which extends into a central chamber 156a formed in a cover 156. Central chamber 156a is here slightly larger than chamber 34 of the previously described embodiment so as to accommodate the dual chamber fluid reservoir. As before, cover 156 includes a plurality of conformable ullages of the character previously described which are in communication via passageways 157.

Figure 13:
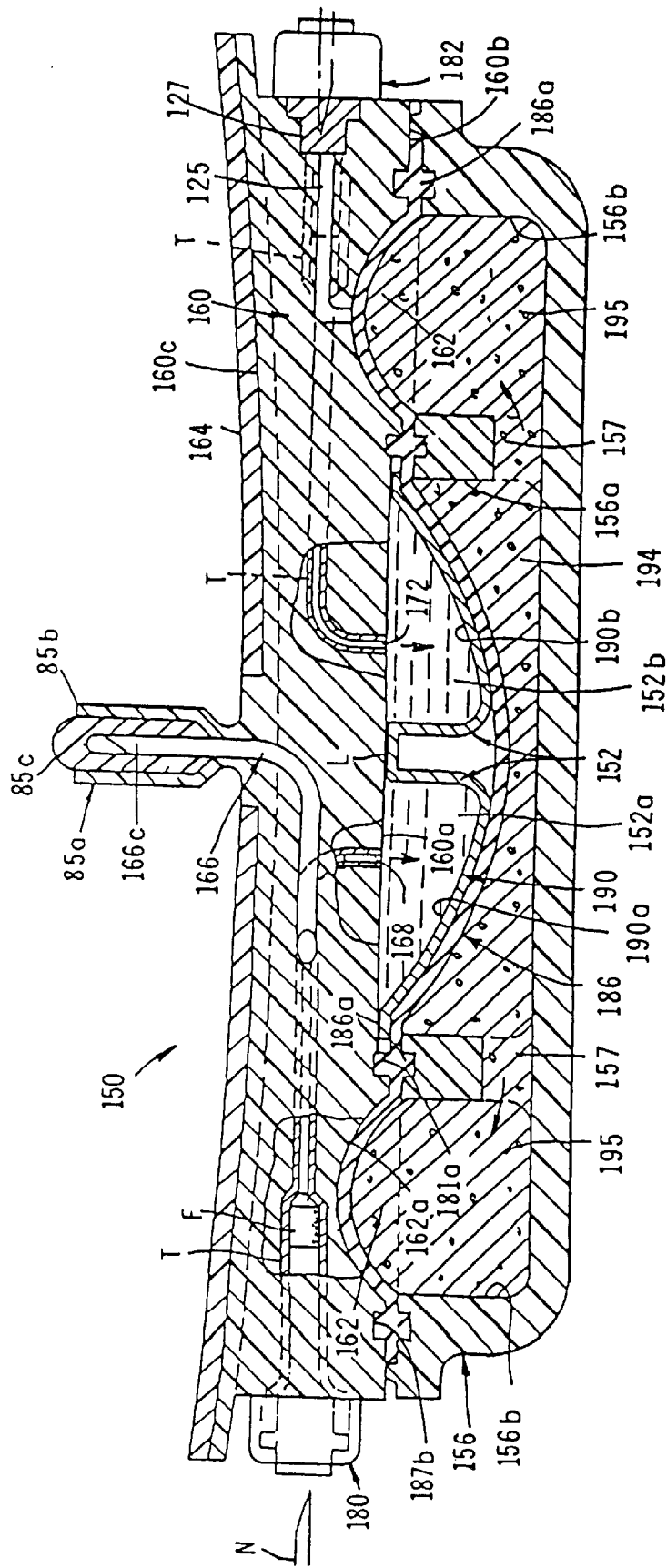
FIG. 13 is an enlarged, cross-sectional view taken along lines 13—13 of FIG. 11.

As best seen in FIGS. 11 and 13, base 160 of this embodiment is of a slightly different construction having first and second filling means for separately filling the dual reservoirs 152a, and 152b. Like the earlier described embodiment, base 160 has a central, surface 160a and a peripheral portion 160b which includes a generally toroidal-shaped expansion channel or groove 162 formed within base 160 and defined by concave surface 162a. In this latest form of the invention, portion 160a is generally planar in shape. Base 160 also has a surface 160c to which an adhesive pad assembly 164 is affixed. Integrally molded within base 160 is a uniquely-shaped hollow cannula 166 (FIG. 17), which comprises a part of the infusion means of this form of the invention.

Figure 12:
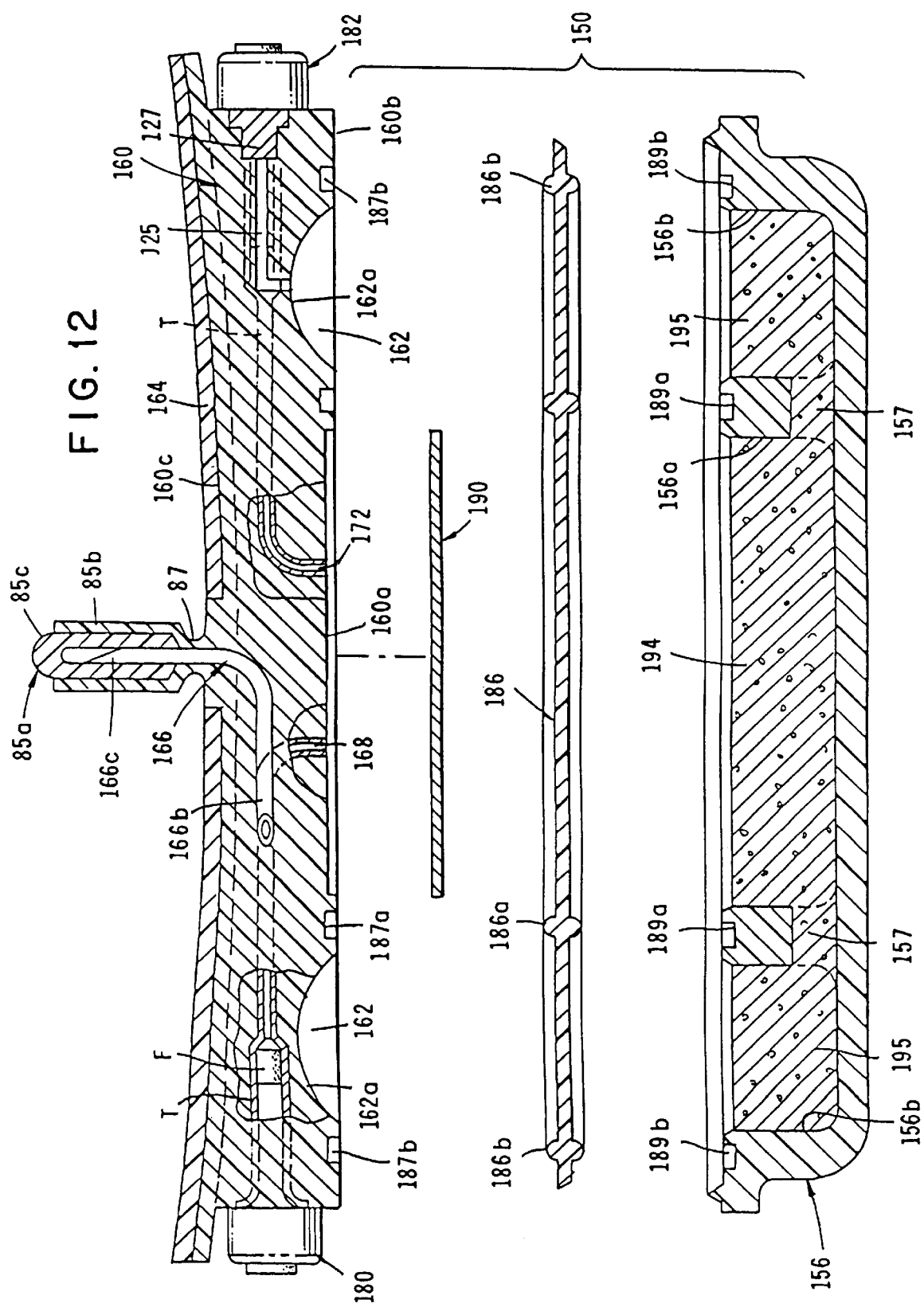
FIG. 12 is an exploded, cross-sectional view of the form of the invention shown in FIG. 11 illustrating the base portion of the apparatus superimposed over the rate control device, the distendable membrane, and the cover of the apparatus.
Figure 14:
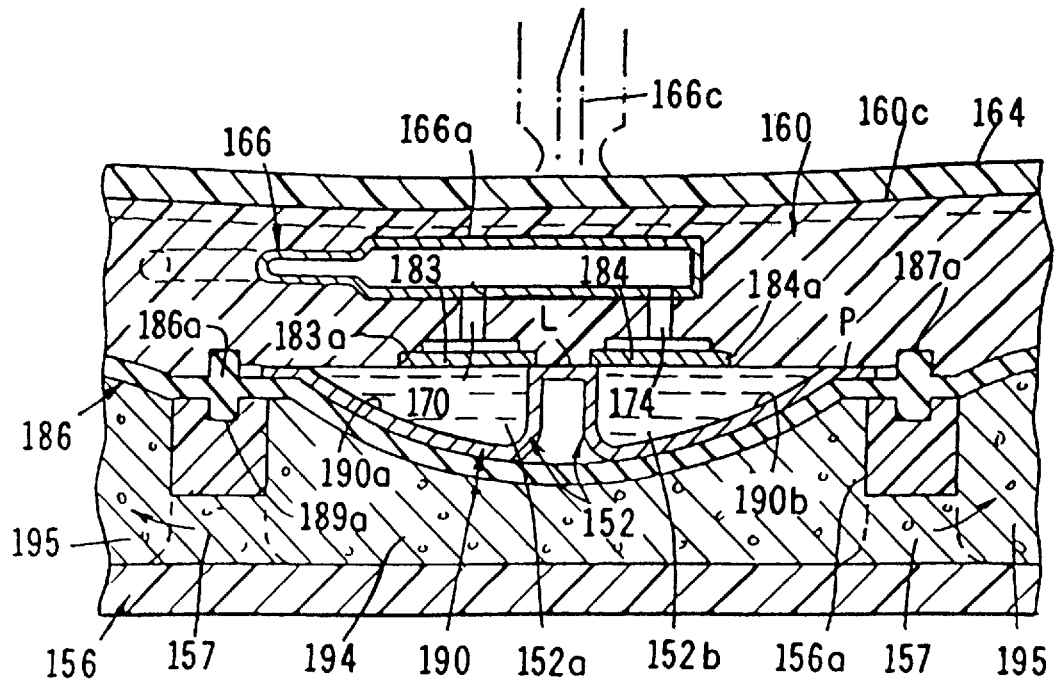
FIG. 14 is an enlarged fragmentary, cross-sectional view of the central portion of the device.

The apparatus shown in FIGS. 11 through 14 includes a uniquely configured stored energy means very similar to that previously described and, in conjunction with the central portion 160a of the base, forms the two fluid reservoirs 152a and 152b. As best seen in FIGS. 11, 12, and 14, fluid reservoir 152a has an inlet port 168 and an outlet port 170. Similarly, fluid reservoir 152b has an inlet port 172 and an outlet port 174. Outlet ports 170 and 174 communicate with inlet ports 175 and 177 respectively provided in enlarged diameter portion 166a of cannula 166 (FIG. 17). Filling of reservoir 152a is accomplished via a first septum assembly 180 of the character previously described, while fluid reservoir 152b is filled via septum assembly 182. As best seen in FIG. 17, each of the septum assemblies communicate with an elongated tubular member "T" which terminates at the inlets of fluid reservoirs 152a and 152b.

In this latest form of the invention, flow control means are provided in the form of first and second rate control membranes 183 and 184 respectively which are disposed within cavities 183a and 184a formed in base 160 proximate outlets 170 and 174. Membranes 183 and 184 can be constructed from a polycarbonate material or, alternatively, can be formed from a hydrogel material of the character previously described.

As in the earlier described form of the invention, the stored energy means or membrane 186, overlays the base and includes an inner O-ring like protuberance 186a and a radially spaced, outer O-ring like protuberance 186b. These O-ring like protuberance are sealably received within generally circular-shaped, radially spaced inner and outer O-ring grooves 187a and 187b formed in base 160 (see FIGS. 12 and 13). When the apparatus is assembled in the manner shown in FIG. 13, membrane 186 spans the central portion of the base as well as the circumferentially extending grooved outer portions 160b. The inner and outer O-ring like portions are also sealably receivable within O-ring grooves 189a and 189b formed in cover 156 (FIG. 12).

Provided in the construction shown in FIGS. 13 and 14, is a highly novel separation means, shown here as a yieldable barrier or separation membrane 190. As best seen in FIG. 11, membrane 190 is bonded to the base along the periphery "P" thereof and along a central dividing line "L" that divides the membrane into first and second portions 190a and 190b. More particularly, the membrane is bonded to the base along the bond areas designated as 191. Areas 191 circumscribes central portion 160a while area 191b bisects the central portions. With this novel construction, as fluid under pressure is introduced into the device via the first and second filling means enters both the stored energy membrane 186 and the separation membrane 190 will deform outwardly in the manner shown in FIG. 13 to form the two fluid reservoirs. As before, the ullage means are covered by distendable membrane 186 and both continuously vary in shape as the distendable membrane distends outwardly from the base as fluid is introduced into reservoirs 152a and 152b via septum assemblies 180 and 182. Once again, the central conformable ullage 194 communicates with the outer toroidal ullage 195 via passageways 157 so that, as fluid chambers 152a and 152b are filled, the gel which makes up the central ullage contained within central chamber 156a is engaged by membrane 186 urging it outward and causing it to flow into toroidal chamber 156b of cover 156. This causes the gel contained within this chamber, along with membrane 186 to, in turn, expand into channel 162 formed in base 160 in the manner shown in FIG. 13. As before, gases contained in this channel will be vented via passageway 125 and vent plug 127. As the fluid is expelled from the reservoirs, the gel will return to central chamber 156a in the manner shown in FIG. 15.

Turning particularly to FIGS. 14 and 16, the uniquely-shaped cannula 166 of the device there illustrated includes the previously identified enlarged diameter portion 166a and the smaller diameter portion 166b which terminates in a needle-like outboard extremity 166c. Cannula 166 is molded in place with a base 160 in a manner well known by those skilled in the art.

Prior to joining the cover and the base as by adhesive bonding or sonic welding and, prior to positioning the distendable membrane over the cover, chambers 156a and 156b are filled with gel. Also, rate control membranes 183 and 184 are, at this time, emplaced into cavities 183a and 184b and separation membrane 190 is adhesively bonded to base 160 along bond areas 191a and 191b. When the cover and base are sealably joined together, the O-ring protuberances 186a and 186b are guided into sealable engagement with grooves 187a and 187b respectively so as to seal distendable membrane 186 relative to the base. If desired, a suitable adhesive can be placed within the grooves to bond the O-ring-like protuberances to the base and to the cover to enhance sealing. After the cover and base have been interconnected, conformable ullages 194 and 195 are sealably captured between distendable membrane 186 and the inner surfaces of cover 156 which define chambers 156a and 156b.

Following the interconnection of base 160 with cover 156 in the manner described in the preceding paragraphs, fluid reservoir 152a can be filled via septum assembly 180 using a suitable syringe assembly containing the beneficial agent to be delivered to the patient. As the fluid is introduced via septum assembly 180 and tube "T", it will impinge upon portion 190a of membrane 190 causing it, along with a portion of distendable membrane 186, to distend outwardly to form reservoir 152a. In similar fashion, fluid reservoir 152b can be filled via septum assembly 182. Once again, as fluid is introduced into the device via septum assembly 182, and tube "T", it will impinge upon portion 190b of membrane 190 causing it, along with a portion of distendable membrane 186, to distend outwardly to form reservoir 152b. As the central portion of the distendable membrane 186 thusly extends outwardly, the peripheral portion thereof will extend into channel 162 in the manner shown in FIG. 13. Fluid flowing into reservoirs 152a and 152b will be filtered by filter means shown here as porous filters "F" which are carried within tubes "T".

Figure 15:
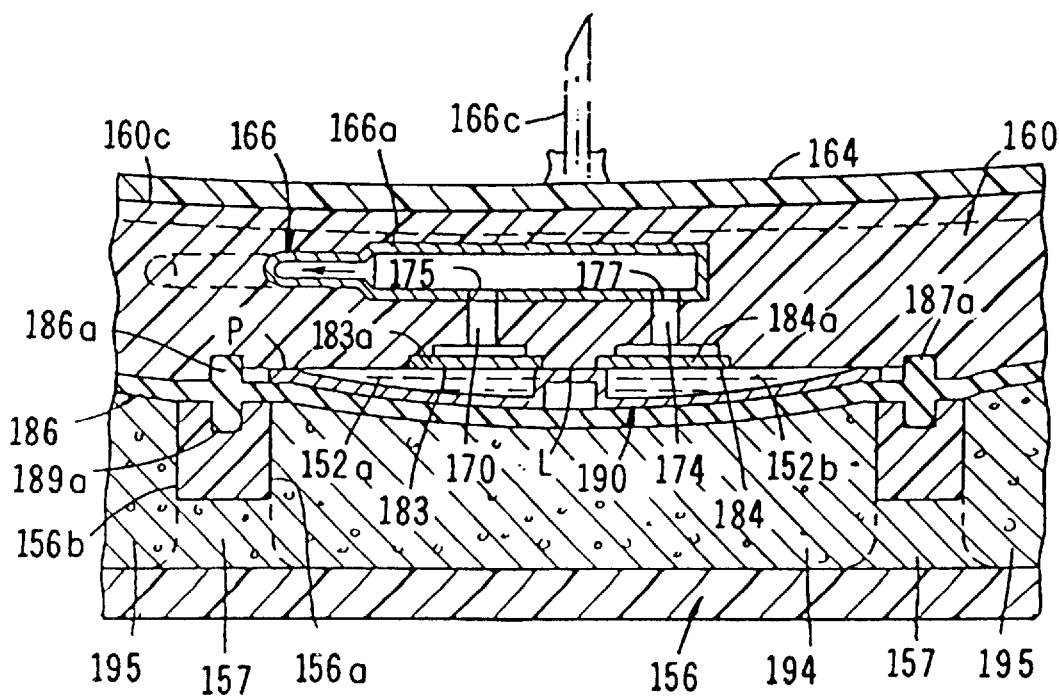
FIG. 15 is a fragmentary, cross-sectional view similar to FIG. 14, but showing fluid being expelled from the fluid reservoir of the device.

As fluid is dispelled from reservoirs 152a and 152b in the manner shown in FIG. 15, the central portion of the distendable membrane will move toward the central portion of the base causing fluid to flow into inlet ports 175 and 177 of the cannula via rate controls 183 and 184. At the same time, the peripheral portion of the distendable membrane will cause conformable mass 195 to flow toward central chamber 156a in the manner shown in FIG. 15.

It will be appreciated that reservoirs 152 and 152b can be filled with the same or different fluids. Further, the rate flow of the fluids from the two reservoirs can be precisely regulated as desired by proper selection of the rate control means or member 183 and 184.

Turning next to FIGS. 18 through 26, another form of the ultra low profile infusion device of the present invention is there shown and generally designated by the numeral 200. This latest embodiment of the invention is similar in some respects to the embodiment shown in FIGS. 1 through 5, but comprises a sealing means of different construction for sealably interconnecting the distendable membrane with the base and with the cover. This latest form of the invention also comprises a single fluid reservoir 202 disposed within a central chamber 204 formed in a cover 205 and includes a plurality of conformable ullages which are in communication (FIG. 21). More particularly, the device includes a central conformable ullage defining means, or first conformable mass 206 which is in an inferior position to central fluid reservoir 202, as viewed in FIG. 24, and a toroidal-shaped, conformable ullage defining mass, or second conformable mass 208 circumscribing ullage 206.

As best seen in FIGS. 21 and 24, the apparatus here comprises a base 210 having a first surface 212, including a central portion 212a and a peripheral portion 212b circumscribing central portion 212a. Peripheral portion 212b includes a concave surface 213a which defines a generally toroidal-shaped expansion channel or groove 213 formed within base 210. As before, base 210 is also provided with a second surface 214 to which an adhesive pad assembly 216 is affixed. After a peal strip is removed from the pad assembly to expose a thin adhesive layer "A", the device can be conveniently affixed to the patient's body. Formed within base 210 is a bore 220 (FIG. 18), which receives a portion of the infusion means, or hollow cannula 222, of the invention.

The apparatus shown in FIGS. 18 through 26 also includes a stored energy means for forming, in conjunction with the central portion of the base, the fluid reservoir 202. Fluid reservoir 202 has an inlet port 226 and an outlet port 230. Inlet port 226 is in communication with an outlet port 232a which is provided in an enlarged diameter portion 222a of cannula 222 (FIG. 19). Filling of fluid reservoir 202 is accomplished via a septum assembly 236 of the character previously described having a pierceable septum 236a (FIG. 22). As before, a flow control means comprises the micro bore portion 222b of the cannula. The flow control means in this latest embodiment of the invention also comprises a flow control member 238, the character of which will presently be described.

The stored energy means is here provided in the form of a generally planar distendable membrane 240 which overlays surface 212 of the base. When the apparatus is assembled in the manner shown in FIG. 24, membrane 240 spans central portion 212a as well as the circumferentially extending channeled outer portion 212b of base 210. Membrane 240 is sealably receivable within inner and outer ring-like grooves 243 and 245 which are formed in cover 205 (FIG. 21). Grooves 243 and 245 form a part of the sealing means of this embodiment of the invention as do inner and outer ring-like protuberances 247 and 249 formed on base 210. As best seen by referring to FIG. 24, when base 210 and cover 205 are joined together, protuberance 247 is closely received within groove 243 and protuberance 249 is closely received within groove 245 in a manner to sealably clamp inner and outer ring-like portions 240a and 240b of distendable membrane 240 between base 210 and cover 205.

Disposed within a generally circular shaped recess 254 formed in base 210 is a barrier means or barrier membrane 256 which prevents fluid within fluid reservoir 202 from contacting distendable membrane 240. Membrane 256 can be formed from any suitable elastomeric material such as polyurethane, silicon or synthetic rubber.

With the construction shown in FIG. 24, the central or first conformable mass 206 of the ullage defining means is disposed within chamber 204 for engagement with membrane 240 which, after being distended, will tend to return to its less distended configuration. As was the case with the previously discussed embodiments, the ullage defining means of this latest embodiment of the invention comprises not only the central conformable ullage 206, but also the outer toroidal shaped, conformable ullage 208. Both of the conformable masses 206 and 208 are uniquely covered by distendable membrane 240 and both continuously vary in shape as the distendable membrane distends outwardly from the base (FIG. 24).

As before in this latest embodiment of the invention first conformable mass ullage 206 communicates with the second outer toroidal-shaped mass 208 via passageways 261 which interconnect the first or central chamber 204 formed in cover 205 with the second toroidal-shaped chamber 264 formed in cover 205 (FIG. 21). As before, conformable masses 206 and 208 preferably comprise a deformable, flowable mass constructed from a suitable gel material. Accordingly, in a manner presently to be described, the gel which makes up first conformable mass 206 can expand into chamber 264 formed in cover 205 via passageways 261 as the distendable membrane 240 distends outwardly during fulling of fluid chamber 202.

Turning particularly to FIGS. 18, 19, and 24, the generally straight cannula 222 of the device includes the previously identified enlarged diameter portion 222a and the microbore portion 222b which terminates in an outboard extremity 222c which is suitably interconnected with a luer connector 265. In this latest form of the invention, the cannula is molded in place within bore 220.

Turning particularly to FIG. 21, it can be seen that, as before, cover 205 is provided with an upstanding protuberance 267 which permits joining of the cover 205 to the base 210 by a sonic welding technique of the character previously described. Prior to joining the cover and the base and, prior to positioning the distendable membrane over the cover, chambers 204 and 264 are filled with gel. Also barrier membrane 256 is, at this time, appropriately bonded to the base by adhesive bonding or like techniques well known to those skilled in the art. When the cover and base are sealably joined together, the ring-like protuberances 247 and 249 are guided into grooves 243 and 245 respectively so as to sealably clamp distendable membrane 240 securely between the base and the cover. If desired, a suitable adhesive can be placed within grooves 243 and 245 to bond portions 240a and 240b of the distendable membrane to the cover to enhance sealing. After the cover and base have been interconnected, conformable ullages 206 and 208 are sealably captured between distendable membrane 240 and the inner surfaces of cover 205 which define chambers 204 and 264. It is to be noted that chambers 204 and 256 can also be filled with gel via a fill port 205f and a passageway 205p (see FIG. 24).

Following the interconnection of base 210 with cover 205 in the manner described in the preceding paragraphs, fluid reservoir 202 can be filled via septum assembly 236 using a suitable syringe assembly containing the beneficial agent to be delivered to the patient. As the fluid chamber fills, conformable mass 206 will conform to the central portion of the distendable membrane in the manner shown in FIG. 24 causing the gel which comprises mass 206 to be forced inwardly and to overflow into the second toroidal-shaped chamber 264 via passageways 261. As the gel flows under pressure into chamber 264, the outer peripheral portion of the distendable membrane 240 will deform toward concave surface 213a and into base channel 213 permitting this channel to, at least, partially fill with gel. As the peripheral portion of the distendable membrane distends into channel 213, any gases contained therein will be vented to atmosphere via vent means which here comprises a passageway 269 and a vent plug 271 (see FIGS. 18 and 20).

During the fluid expelling step, the gel can, of course, flow in the opposite direction from toroidal-shaped chamber 264 into first or central chamber 204 so as to conform to distendable membrane 240 as it tends to return toward its less distended configuration.

With chambers 204 and 264 filled with gel, with fluid reservoir 202 filled with the selected beneficial agent to be delivered to the patient and with the luer connector 265 connected to a valved administration line, the device can be safely stored until time of use. At time of use, the administration line can be opened to fluid flow toward the patient.

Turning to FIG. 23 a slightly different form of cannula and septum is there illustrated. Here the fill end of cannula 223 is bell shaped to sealably receive a matching shaped septum 237a. This alternate design is better suited for certain end applications of the device.

Referring now to FIGS. 26 through 32, still another form of the ultra low profile infusion device of the invention is there shown and generally designated by the numeral 300. This latest embodiment of the invention is similar in many respects to the embodiment shown in FIGS. 18 through 25 and like numbers are used to identify like components. This latest embodiment of the invention comprises a single fluid reservoir 302 (FIG. 31) disposed within a first central chamber 204 formed in a cover 205 which is identical to that previously described in connection with the embodiment of FIGS. 18 through 25 and includes conformable masses 206 and 208 of the character previously described which are in communication via passageways 261.

As best seen in FIGS. 29 and 31, base 306 of this embodiment is of a slightly different construction having a central, generally convex surface 306a and a peripheral portion 306b which includes a concave surface 310a which defines a generally toroidal-shaped expansion channel or groove 310 formed within base 306. In this latest form of the invention, convex portion 306a, in cooperation with the conformable masses 206 and 208, comprise the ullage means of the invention. As before, base 306 has a surface 306c to which an adhesive pad assembly 216 is a affixed. Integrally molded within base 306 is a hollow cannula 314, which comprises a part of the infusion means of this form of the invention.

The apparatus shown in FIGS. 26 through 32 includes a uniquely configured stored energy means identical to that described in connection with the embodiment shown in FIGS. 18 through 25 and forms, in conjunction with the central portion 306a of the base, the fluid reservoir 302. Fluid reservoir 302 has an inlet port 316 and an outlet port 320. Inlet port 316 is in communication with an outlet port 314a which is provided in an enlarged diameter portion 314b of cannula 314. Filling of fluid reservoir 302 is accomplished via a septum assembly 236 of the character previously described having a septum 236a.

In this latest form of the invention, flow control means comprises both a uniquely shaped hydrogel rate control device 318 as well as the micro bore portion 314c of the cannula. Rate control device 318 is held in place within a recess 321 formed in base 306 by any suitable means such as adhesive bonding. In use, the hydrogel rate control device swells upon imbibing fluid and functions to precisely control the rate of fluid flow from reservoir 302.

As in the earlier described form of the invention, the stored energy means or membrane 240, overlays the base and is sealably interconnected with cover 205 in the same manner as described in connection with the form of the invention shown in FIGS. 18 through 25. When the apparatus is assembled in the manner shown in FIG. 31, membrane 240 spans the central portion of the base as well as the circumferentially extending channeled outer portion 306b. Inner and outer ring-like protuberances 323 and 325 are sealably receivable within ring-like grooves 243 and 245 which are formed in cover 205 (FIG. 31) and which comprise a part of the sealing means of the invention.

In the construction shown in FIG. 31, the central convex portion 306a of the base forms the rigid ullage portion of the ullage means and ullage portions 206 and 208 form the conformable ullage portions of the ullage means. As before, the conformable ullage portions of the ullage means are covered by distendable membrane 240 and both continuously vary in shape as the distendable membrane distends outwardly from the base as fluid is introduced into reservoir 302 via the septum assembly. Once again, central conformable ullage 206 communicates with the outer toroidal ullage 208 via passageways 261 so that, as fluid chamber 302 is filled, the gel which makes up the central ullage is engaged by a barrier membrane 328 which is disposed between distendable membrane 240 and cover 305. With this construction, as reservoir 302 fills membranes 240, 327, and 328 will distend outwardly in the manner shown in FIG. 31 causing gel 206 to flow into chamber 264 of cover 205. This causes the gel contained within this chamber to, in turn, expand, along with the membrane 240 into channel 310 formed in base 306 in the manner shown in FIG. 31.

As before, as shown in FIG. 28, cannula 314 includes the previously identified enlarged diameter portion 314b and the microbore portion 314c which terminates in an extremity 314d which communicates with a novel quick connect delivery assembly 331, the character of which will presently be described.

Prior to joining the cover and the base as by sonic welding and, prior to positioning the distendable membrane 240 and the containment film 328 over the cover, chambers 204 and 264 are filled with the conformable mass or gel. Containment film 328 can be constructed of various materials such as cellulose acetate, polyethylene, polypropylene, polyvinyl films and the like and functions to contain the mass or gel within the cover. Also, rate control device 318 is, at this time, emplaced into cavity 321 and a first barrier membrane 327 is affixed along its periphery to the central portion of base 306. When the cover and base are sealably joined together, the ring-like protuberances 323 and 325 formed on base 306 are guided into sealable engagement with grooves 243 and 245 respectively so as to sealably clamp both distendable membrane 240 and film 328 between the base and the cover. If desired, a suitable adhesive can be placed within grooves 243 and 245 to bond to the two membranes and to the cover to enhance sealing. After the cover and base have been thusly interconnected, conformable ullages 206 and 208 are sealably captured between containment film 328 and the inner surfaces of cover 205 which define chambers 204 and 264.

Following the interconnection of base 306 with cover 205 in the manner described in the preceding paragraphs, fluid reservoir 302 can be filled via septum assembly 236 using a suitable syringe assembly containing the beneficial agent to be delivered to the patient. Filter means, shown here as a porous filter member 335, filters the fluid flowing out of outlet 314a. Filter 335 can be constructed from any suitable filter material such as a polycarbonate and is backed by a fluid flow blocking means shown here as a blocking membrane 335a. Blocking membrane 335a functions to direct the fluid flowing into cannula portion 314b toward fluid reservoir 302. As the fluid reservoir fills, the peripheral portions of the distendable membrane 240 and the barrier membrane 328 will distend into channel 310, and any gases contained therein will be vented to atmosphere via passageway 206a and vent plug 271 (see FIG. 26). During the fluid expelling step, the gel can, of course, flow in the opposite direction from toroidal chamber 264 into central chamber 204 so as to conform to barrier membrane 328 as it tends, along with the distendable membrane, to return toward their less distended configuration.

Turning particularly to FIG. 30 the novel dispensing means of the form of the invention is there illustrated. this dispensing means includes the previously identified quick connect delivery fitting 331 having a tapered extremity 331a which is telescopically and sealably receivable within a tapered bore 342 form in base 306 (FIG. 29). In order to releasably lock fitting 331 in position within bore 342 and in fluid communication with end 314d of cannula 314, locking means shown here as resiliently deformable locking tabs 344 are provided on base 306. Extending from the outboard end of quick connect fitting assembly 331 is an infusion set 346 having a soft cannula assembly 350, the operation of which is well understood by those skilled in the art. Once the soft cannula 350a has been introduced into the patient's subdermal tissue "ST" in the manner shown in FIG. 30, the cannula insertion assembly 352, which includes a trocar 352a can be removed, leaving the soft cannula 350a in position within the patient. Needle cannula interconnect 354a of the connector assembly 354 of infusion set 346 can then be inserted into assembly 350 and interconnect therewith using the conventional latch mechanism 355. Connector assembly 354 which forms a part of infusion set 346, when connected to assembly 350, places soft cannula 350a in fluid communication with reservoir 302. Infusion set 346 is of a character well known in the art and is readily available from several commercial sources including Pharma-Plast International A/S, Lynge Denmark. By pushing inwardly on member 334, delivery quick connect 331 can be urged into tapered bore 342 to a position wherein locking tabs 344 will close about member 344 and in engagement with a shoulder 331a formed on member 331 so as to securely lock the infusion means of the invention to the base.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. An ultra low profile device for use in infusing medicinal fluid into a patient at a controlled rate comprising:
   (a) a thin base having an upper surface including a central portion and a peripheral portion circumscribing said central portion, a lower surface engageable with the patient and a circuitous channel formed in said base intermediate said upper and lower surface, portions of said channel being disposed beneath said central portion and said peripheral portion, said channel having first and second ends;
   (b) stored energy means for forming in conjunction with said base, a first reservoir having a fluid inlet and a fluid outlet, said stored energy means comprising at least one distendable membrane superimposed over said base, said membrane being distendable as a result of pressure imparted by fluids introduced into said first reservoir to establish internal stresses, said stresses tending to move said membrane toward a less distended configuration;
   (c) a cover connected to said base, said cover having a first chamber and a second chamber circumscribing said first chamber and at least one passageway interconnecting said first and second chambers;
   (d) a first ullage defining means for providing ullage within said first reservoir, said first ullage defining means comprising a conformable mass disposed within said first chamber of said cover;
   (e) a second ullage defining means said second ullage defining means comprising a conformable mass disposed within said second chamber of said cover;
   (f) first fill means in communication with said inlet of said first reservoir for filing said first reservoir; and
   (g) infusion means for infusing medicinal fluid from said first reservoir into the patient, said infusion means comprising a hollow cannula having:
      (i) a body portion disposed within said circuitous channel formed in said base; and
      (ii) an outlet end provided in the form of a pierceable portion extending perpendicularly outwardly from said second end of said channel for insertion into the patient.

2. A device as defined in claim 1 further including flow control means for controlling the rate of fluid flow from said first reservoir, said flow control means comprising a hydrogel rate control device disposed between said fluid outlet of said first reservoir and said infusion means.

3. A device as defined in claim 1 further including a barrier membrane connected to said central portion of said base, said barrier membrane being disposed between said distendable membrane and said base and being distendable by fluid introduced by said first fill means.

4. A device as defined in claim 3 in which said barrier membrane includes a peripheral boundary and a center line dividing said barrier membrane into first and second portions, said barrier membrane being connected to said base along said peripheral boundary and along said center line, said first portion cooperating with said base and said distendable membrane to form said first reservoir.

5. A device as defined in claim 4 further including:
   (a) a second reservoir formed by said second portion of said barrier membrane in cooperation with said base and said distendable membrane; said second reservoir having a fluid inlet and a fluid outlet in communication with said infusion means; and
   (b) second fill means in communication with said inlet of said second reservoir for filling said second reservoir.

6. A device as defined in claim 5 in which said first and second fill means comprises spaced-apart first and second pierceable septums mounted within said base.

7. A device as defined in claim 5 further including (flow control means ) for controlling the rate of fluid flowing from said first and second reservoirs toward said infusion means.

8. A device as defined in claim 7 in which said hollow cannula includes an enlarged diameter portion having a first inlet port in communication with said outlet of said first reservoir and a second inlet port in communication with said outlet of said second reservoir and in which said flow control means comprises first and second rate control devices disposed between said first and second inlet ports of said enlarged diameter portion of said cannula and said outlets of said first and second reservoirs.

9. A device as defined in claim 7 in which a portion of said first ullage means is urged from said first chamber of said cover toward said second chamber of said cover via said passageway as said distendable membrane and said barrier membrane are distended by fluid entering the device via said first and second fill means.

\* \* \* \* \*